US006482802B1

(12) United States Patent
Hu et al.

(10) Patent No.: US 6,482,802 B1
(45) Date of Patent: Nov. 19, 2002

(54) USE OF NEOMYCIN FOR TREATING ANGIOGENESIS-RELATED DISEASES

(75) Inventors: Guo-fu Hu, Brookline, MA (US); Bert L. Vallee, Boston, MA (US)

(73) Assignee: Endowment for Research in Human Biology, Inc., Boston, MA (US)

( * ) Notice: Subject to any disclaimer, the term of this patent is extended or adjusted under 35 U.S.C. 154(b) by 0 days.

(21) Appl. No.: 09/700,436

(22) PCT Filed: May 11, 1999

(86) PCT No.: PCT/US99/10269

§ 371 (c)(1),
(2), (4) Date: Nov. 9, 2000

(87) PCT Pub. No.: WO99/58126

PCT Pub. Date: Nov. 18, 1999

Related U.S. Application Data

(60) Provisional application No. 60/084,921, filed on May 11, 1998.

(51) Int. Cl.⁷ ............................................... A61K 31/37

(52) U.S. Cl. ............................ 514/39; 514/2; 536/13.2

(58) Field of Search ........................... 514/39; 536/13.2

(56) References Cited

U.S. PATENT DOCUMENTS

| 2,799,620 A | 7/1957 | Waksman | 167/65 |
|---|---|---|---|
| 5,135,919 A | 8/1992 | Folkman et al. | 514/56 |
| 5,135,920 A | 8/1992 | Kanamaru et al. | 514/59 |
| 5,639,725 A | 6/1997 | O'Reilly et al. | 514/12 |
| 5,698,586 A | 12/1997 | Kishimoto et al. | 514/475 |
| 5,712,291 A | 1/1998 | D'Amato | 514/323 |

FOREIGN PATENT DOCUMENTS

WO  WO 97/35567  10/1997

OTHER PUBLICATIONS

Akselband Y, Harding MW, Nelson PA. Rapamycin inhibits spontaneous and fibroblast growth factor beta–stimulated proliferation of endothelial cells and fibroblasts. Transplant Proc. Dec. 1991;23(6):2833–6.
Baldin V, Roman AM, Bosc–Bierne I, Amalric F, Bouche G. Translocation of bFGF to the nucleus is G1 phase cell cycle specific in bovine aortic endothelial cells. EMBO J. May 1990;9(5):1511–7.
Beck L Jr, D'Amore PA. Vascular development: cellular and molecular regulation. FASEB J. Apr. 1997;11(5):365–73.
Bicknell R, Vallee BL. Angiogenin activates endothelial cell phospholipase C. Proc Natl Acad Sci U S A. Aug 1988;85(16):5961–5.
Blaser J, Triebel S, Kopp C, Tschesche H. A highly sensitive immunoenzymometric assay for the determination of angiogenin. Eur J Clin Chem Clin Biochem. Aug. 1993;31(8):513–6.

Bouche G, Gas N, Prats H, Baldin V, Tauber JP, Teissie J, Amalric F. Basic fibroblast growth factor enters the nucleolus and stimulates the transcription of ribosomal genes in ABAE cells undergoing G0—G1 transition. Proc Natl Acad Sci U S A. Oct. 1987;84(19):6770–4.
Chopra V, Dinh TV, Hannigan EV. Angiogenin, Interleukins, and Growth–Factor Levels in Serum of Patients with Ovarian Cancer: Correlation with Angiogenesis, Cancer J Sci Am. Oct. 1996;2(5):279.
Colville–Nash PR, Alam CA, Appleton I, Brown JR, Seed MP, Willoughby DA. The pharmacological modulation of angiogenesis in chronic granulomatous inflammation. J Pharmacol Exp Ther. Sep. 1995;274(3):1463–72.
Crum R, Szabo S, Folkman J. A new class of steroids inhibits angiogenesis in the presence of heparin or a heparin fragment. Science. Dec. 20, 1985;230(4732):1375–8.
D'Amato RJ, Lin CM, Flynn E, Folkman J, Hamel E. 2–Methoxyestradiol, an endogenous mammalian metabolite, inhibits tubulin polymerization by interacting at the colchicine site. Proc Natl Acad Sci U S A. Apr. 26, 1994;91(9):3964–8.
D'Amato RJ, Loughnan MS, Flynn E, Folkman J. Thalidomide is an inhibitor of angiogenesis. Proc Natl Acad Sci U S A. Apr. 26, 1994;91(9):4082–5.
Fett JW, Strydom DJ, Lobb RR, Alderman EM, Bethune JL, Riordan JF, Vallee BL. Isolation and characterization of angiogenin, and angiogenic protein from human carcinoma cells. Biochemistry. Sep. 24, 1985;24(20):5480–6.
Fett JW, Olson KA, Rybak SM. A monoclonal antibody to human angiogenin. Inhibition of ribonucleolytic and angiogenic activities and localization of the antigenic epitope. Biochemistry. May 10, 1994;33(18):5421–7.
Folkman J. Fighting cancer by attacking its blood supply. Sci Am. Sep. 1996;275(3):150–4.
Folkman J, Langer R, Linhardt RJ, Haudenschild C, Taylor S. Angiogenesis inhibition and tumor regression caused by heparin or a heparin fragment in the presence of cortisone. Science. Aug. 19, 1983;221(4612):719–25.
Folkman J. Tumor angiogenesis:therapeutic implications. N Engl J Med. Nov. 18, 1971;285(21):1182–6.
Folkman J, Shing Y Angiogenesis. J Biol Chem Jun. 5, 1992;267(16):10931–4.

(List continued on next page.)

Primary Examiner—Richard L. Raymond
(74) Attorney, Agent, or Firm—Pennie & Edmonds LLP

(57) ABSTRACT

The present invention is directed to using neomycin or an analogue thereof as an therapeutic agent to treat angiogenesis-related diseases, which are characterized by excessive, undesired or inappropriate angiogenesis or proliferation of endothelial cells. The present invention is also directed to pharmaceutical compositions comprising (a) neomycin or an analogue and, optionally, (b) another anti-angiogenic agent or an anti-neoplastic agent. The present invention is further directed to a method for screening neomycin analogues having anti-angiogenic activity. A preferred embodiment of the invention relates to using neomycin to treat subjects having such diseases.

63 Claims, 4 Drawing Sheets

OTHER PUBLICATIONS

Figure 1:
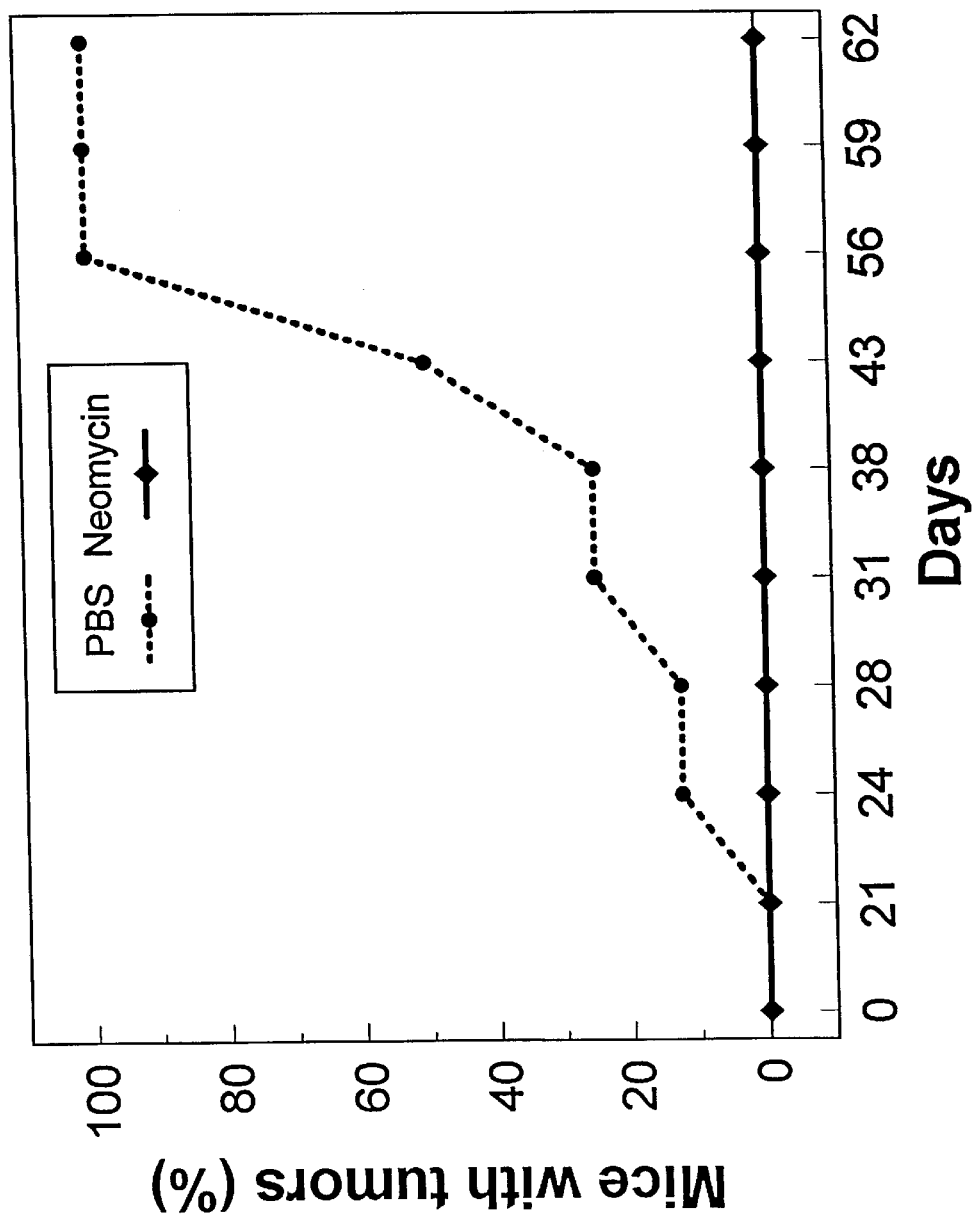

Gho YS, Lee JE, Oh KS, Bac DG, Chae CB. Development of antiangiogenin peptide using a phage–displayed peptide library. Cancer Res. Sep. 1, 1997;57(17):3733–40.

Gho YS, Chae CB. Anti–angiogenin activity of the peptides complementary to the receptor–binding site of angiogenin. J Biol Chem. Sep. 26, 1997;272(39):24294–9.

Gimbrone MA Jr, Cotran RS, Leapman SB, Folkman J. Tumor growth and neovascularization: an experimental model using the rabbit cornea. J Natl Cancer Inst. Feb. 1974;52(2):413–27.

Hallahan TW, Shapiro R, Strydom DJ, Vallee BL. Importance of asparagine–61 and asparagine–109 to the angiogenic activity of human angiogenin. Biochemistry. Sep. 1, 1992;31(34):8022–9.

Hallahan TW, Shaprio R, Vallee BL. Dual site model for the organogenic activity of angiogenin. Proc Natl Acad Sci U S A. Mar. 15, 1991;88(6):2222–6.

Hildebrandt JP, Plant TD, Meves H. The effects of bradykinin on K+ currents in NG108–15 cells treated with U 73122, a phospholipase C inhibitor, or neomycin. Br J Pharmacol. Mar. 1997;120(5):841–50.

Hu GF, Chang SI, Riordan JR, Vallee BL. An angiogenin–binding protein from endothelial cells. Proc Natl Acad Sci U S A. Mar. 15, 1991;88(6):2227–31.

Hu GF, Strydom DJ, Fett JW, Riordan JF, Vallee BL. Actin is a binding protein for angiogenin. Proc Natl Acad Sci U S A. Feb. 15, 1993;90(4):1217–21.

Hu GF, Riordan JF, Vallee BL. A putative angiogenin receptor in angiogenin–responsive human endothelial cells. Proc Natl Acad Sci U S A. Mar. 18, 1997;94(6):2204–9.

Hu G, Riordan JF, Vallee BL. Angiogenin promotes invasiveness of cultured endothelial cells by stimulation of cell–associated proteolytic activities. Proc Natl Acad Sci U S A. Dec. 6, 1994;91(25):12096–100.

Ingber D, Fujita T, Kishimito S, Sudo K, Kanamaru T, Brem H, Folkman J. Synthetic analogues of fumagillin that inhibit angiogenesis and suppress tumour growth. Nature, Dec. 6, 1990;348(6301):555–7.

Jimi S, Ito K, Kohno K, Ono M, Kuwano M, Itagaki Y, Ishikawa H. Modulation by bovine angiogenin of tubular morphogenesis and expression of plasminogen activator in bovine endothelial cells. Biochem Biophys Res Commun. Jun. 15, 1995;211(2):476–83.

Kimura M, Suzuki J, Amemiya K. Mouse granuloma pouch induced by Freund's complete adjuvant with croton oil, J Pharmacobiodyn. Jun. 1985;8(6):393–400.

Knighton D, Ausprunk D, Tapper D, Folkman J. Avascular and vascular phases of tumour growth in the chick embryo. Br J Cancer. Mar. 1977;35(3):347–56.

Lee FS, Fox EA, Zhou HM, Strydom DJ, Vallee BL. Primary structure of human placental ribonuclease inhibitor. Biochemistry, Nov. 15, 1988;27(23):8545–53.

Leek RD, Harris AL, Lewis CE. Cytokine networks in solid human tumors: regulation of angiogenesis. J Leukoc Biol. Oct. 1994;56(4):423–35.

Li D, Bell J, Brown A, Berry CL. The observation of antigenin and basic fibroblast growth factor gene expression in human colonic adenocarcinomas, gastric adenocarcinomas, and hepatocellular carcinomas. Pathol. Feb. 1994;172(2):171–5.

Li R, Riordan JF. Hu G. Nuclear translocation of human angiogenin in cultured human umbilical artery endothelial cells is microtubule and lysosome independent. Biochem Biophys Res Commun. Sep. 18, 1997;238(2):305–12.

Maione TE, Gray GS, Petro J, Hunt AJ, Donner AL, Bauer SI, Carson HF, Sharpe RJ. Inhibition of angiogenesis by recombinant human platelet factor–4 and related peptides. Science. Jan. 5, 1990;247(4938):77–9.

Matsubara T, Saura R, Hirohata K, Ziff M. Inhibition of human endothelial cell proliferation in vitro and neovascularization in vivo by D–penicillamine. J Clin Invest. Jan. 1989;83(1):158–67.

Moroianu J, Riordan JF. Nuclear translocation of angiogenin in proliferating endothelial cells is essential to its angiogenic activity, Proc Natl Acad Sci U S A. Mar. 1, 1994;91(5):1677–81.

Moroianu J, Riordan JF. Identification of the nucleolar targeting signal of human angiogenin. Biochem Biophys Res Commun. Sep. 30, 1994;203(3):1765–72.

Moses MA, Sudhalter J, Langer R. Identification of an inhibitor of neovascularization from cartilage. Science. Jun. 15, 1990;248(4961):1408–10.

Moses MA, Langer R. Inhibitors of angiogenesis. Biotechnology (N Y). Jul. 1991;9(7):630–4.

Nozaki Y, Hida T, Iinuma S, Ishii T, Sudo K, Muroi M, Kanamaru T. TAN–1120, a new anthracycline with potent angiostatic activity, J Antibiot (Tokyo). Apr. 1993;46(4):569–79.

O'Reilly MS, Boehm T, Shing Y, Fukai N, Vasios G, Lane WS, Flynn E, Birkhead JR, Olsen BR, Folkman J. Endostatin: an endogenous inhibitor of angiogenesis and tumor growth. Cell. Jan. 24, 1997;88(2):277–85.

O'Reilly MS, Holmgren L, Shing Y, Chen C, Rosenthal RA, Moses M, Lane WS, Cao Y, Sage EH, Folkman J. Angiostatin: a novel angiogenesis inhibitor that mediates the suppression of metastases by a Lewis lung carcinoma. Cell. Oct. 21, 1994;79(2):315–28.

Oikawa T, Hasegawa M, Shimamura M, Ashino H, Murota S, Morita I. Eponemycin, a novel antibiotic, is a highly powerful angiogenesis inhibitor. Biochem Biophys Res Commun. Dec. 31, 1991;181(3):1070–6.

Oikawa T, Hiragun A, Yoshida Y, Ashino–Fuse H, Tominaga T, Iwaguchi T. Angiogenic activity of rat mammary carcinomas induced by 7,12–dimethylbenz[a]anthracene and its inhibition by medroxyprogesterone acetate: possible involvement of antiangiogenic action of medroxyprogesterone acetate in its tumor growth inhibition. Cancer Lett. Dec. 1, 1988;43(1–2):85–92.

Oikawa T, Hirotani K, Shimamura M, Ashino–Fuse H, Iwaguchi T. Powerful antiangiogenic activity of herbimycin A (named angiostatic antibiotic), J Antibiot (Tokyo). Jul. 1989;42(7):1202–4.

Oikawa T, Yoshida Y, Shimamura M, Ashino–Fuse H, Iwaguchi T, Tominaga T. Antitumor effect of 22–oxa–1 alpha,25–dihydroxyvitamin D3, a potent angiogenesis inhibitor, on rat mammary tumors induced by 7,12–dimethylbenz[a]anthracene, Anticancer Drugs, Oct. 1991;2(5):475–80.

Oikawa T, Shimamura M, Ashino–Fuse H, Iwaguchi T, Ishizuka M, Takeuchi T. Inhibition or angiogenesis by 15–deoxyspergualin. J Antibiot (Tokyo). Sep. 1991;44(9):1033–5.

Oikawa T, Hirotani K, Ogasawara H, Katayama T, Nakamura O, Iwaguchi T, Hiragun A. Inhibition of angiogenesis by vitamin D3 analogues. Eur J Pharmacol. Mar. 20, 1990;178(2):247–50.

Oikawa T, Hirotani K, Nakamura O, Shudo K, Hiragun A, Iwaguchi T. A highly potent antiangiogenic activity of retinoids. Cancer Lett. Nov. 30, 1989;48(2):157–62.

Oikawa T, Ashino–Fuse H, Shimamura M, Koide U, Iwaguchi T. A novel angiogenic inhibitor derived from Japanese shark cartilage (I). Extraction and estimation of inhibitory activities toward tumor and embryonic angiogenesis. Cancer Lett. Jun. 15, 1990;51(3):181–6.

Olson KA, French TC, Vallee BL, Fett JW. A monoclonal antibody to human angiogenin suppresses tumor growth in athymic mice. Cancer Res. Sep. 1, 1994;54(17):4576–9.

Olson KA, Fett JW, French TC, Key ME, Vallee BL. Angiogenin antagonists prevent tumor growth in vivo. Proc Natl Acad Sci U S A. Jan. 17, 1995;92(2):442–6.

Piccoli R, Olson KA, Vallee BL, Fett JW. Chimeric anti–angiogenin antibody cAb 26–2F inhibits the formation of human breast cancer xenografts in athymic mice. Proc Natl Acad Sci U S A. Apr. 14, 1998;95(8):4579–83.

Pike SE, Yao L, Jones KD, Cherney B, Appella E. Sakaguchi K, Nakhasi H, Teruya–Feldstein J, Wirth P, Gupta G, Tosato G. Vasostatin, a calreticulin fragment, inhibits angiogenesis and suppresses tumor growth. J Exp Med. Dec. 21, 1998;188(12):2349–56.

Quarto N, Finger FP, Rifkin DB. The NH2–terminal extension of high molecular weight BFGF is a nuclear targeting signal. J Cell Physiol. May 1991;147(2):311–8.

Rybak SM, Auld DS, St Clair DK, Yao QZ, Fett JW. C–terminal angiogenin peptides inhibit the biological and enzymatic activities of angiogenin. Biochem Biophys Res Commun. Jul. 14, 1989;162(1):535–43.

Sano H, Forough R, Maier JA, Case JP, Jackson A, Engleka K, Maciag T, Wilder RL. Detection of high levels of heparin binding growth factor–1 (acidic fibroblast growth factor) in inflammatory arthritic joints. J Cell Biol. Apr. 1990;110(4):1417–26.

Savion N, Vlodavsky I, Gospodarowicz D. Nuclear accumulation of epidermal growth factor in cultured bovine corneal endothelial and granulosa cells. J Biol Chem. Feb. 10, 1981;256(3):1149–54.

Shapiro R, Vallee BL. Human placental ribonuclease inhibitor abolishes both angiogenic and ribonucleolytic activities of angiogenin. Proc Natl Acad Sci U S A. Apr. 1987;84(8):2238–41.

Shapiro R, Riordan JF, Vallee BL. Characteristic ribonucleolytic activity of human angiogenin. Biochemistry. Jun. 17, 1986;25(12):3527–32.

Shapiro R, Vallee BL. Site–directed mutagenesis of histidine–13 and histidine–114 of human angiogenin. Alanine derivatives inhibit angiogenin–induced angiogenesis. Biochemistry. Sep. 5, 1989;28(18):7401–8.

Shimoyama S, Guansuage F, Gansuage S, Negri G. Oohara T, Beger HG. Increased angiogenin expression in pancreatic cancer is related to cancer aggresiveness. Cancer Res. Jun. 15, 1996;56(12):2703–6.

Sornjen D, Kohen F, Lieberherr M. Nongenomic effects of an anti–idiotypic antibody as an estrogen numetic in female human and rat osteoblasts. J Cell Biochem. Apr. 1997;65(1):53–66.

Sugawara K, Hatori M, Nishiyama Y, Tomita K, Kamei H, Konishi M, Oki T. Eponemycin, a new antibiotic active against B16 melanoma. I. Production, isolation, structure and biological activity. J Antibiot (Tokyo). Jan. 1990;43(1):8–18.

Vallee BL, Riordan JF. Organogenesis and angiogenin. Cell Mol Life Sci. Oct. 1997;53(10):803–15.

USE OF NEOMYCIN FOR TREATING ANGIOGENESIS-RELATED DISEASES

This application is a 371 of PCT/US99/10209, filed May 16, 1999 and claims benefit under 35 U.S.C. §119 of U.S. Provisional Application No. 60/084,921 filed May 11, 1998.

1. FIELD OF THE INVENTION

The present invention is directed to a method for treating subjects having an angiogenesis-related disease by administering neomycin or an analogue thereof. The present invention is also directed to a pharmaceutical composition comprising (a) neomycin or an analogue thereof, and, optionally, (b) another anti-angiogenic agent or an anti-cancer agent. The invention is further directed to a method for screening neomycin analogues having anti-angiogenic activity. In a preferred embodiment, neomycin is administered to subjects having angiogenesis-related diseases. In other embodiments, neomycin or an analogue thereof is administered with another anti-angiogenic agent. In additional embodiments, neomycin or an analogue thereof is administered with an anti-neoplastic agent to treat subjects having an angiogenesis-related disease which is a cancer.

2. BACKGROUND OF THE INVENTION

2.1. Angiogensis

Angiogenesis is the complex process of blood vessel formation. The process involves both biochemical and cellular events, including (1) activation of endothelial cells (ECs) by an angiogenic stimulus; (2) degradation of the extracellular matrix, invasion of the activated ECs into the surrounding tissues, and migration toward the source of the angiogenic stimulus; (3) proliferation and differentiation of ECs to form new blood vessels (See, e.g., Folkman et al., 1991, J. Biol. Chem. 267:10931–10934).

The control of angiogenesis is a highly regulated process involving angiogenic stimulators and inhibitors. In healthy humans and animals, angiogenesis occurs under specific, restricted situations. For example, angiogenesis is normally observed in fetal and embryonal development, development and growth of normal tissues and organs, wound healing, and the formation of the corpus luteum, endometrium and placenta.

2.2. Angiogenesis-Related Diseases

The control of angiogenesis is altered in certain diseases. Many such diseases involve pathological angiogenesis (i.e., inappropriate, excessive or undesired blood vessel formation), which supports the disease state and, in many instances, contributes to the cellular and tissue damage associated with such diseases. Angiogenesis-related diseases (i.e., those involving pathological angiogenesis) are myriad and varied. They include, but are not limited to, various forms of tumors, chronic inflammatory diseases, and neovascularization diseases.

The formation and metastasis of tumors involve pathological angiogenesis. Like healthy tissues, tumors require blood vessels in order to provide nutrients and oxygen and remove cellular wastes. Thus, pathological angiogenesis is critical to the growth and expansion of tumors. Tumors in which angiogenesis is important include solid tumors as well as benign tumors such as acoustic neuroma, neurofibroma, trachoma and pyogenic granulomas.

Pathological angiogenesis also plays an important role in tumor metastasis. Pathological angiogenesis is important in two aspects. In one, the formation of blood vessels in tumors allows tumor cells to enter the blood stream and to circulate throughout the body. In the other, angiogenesis supports the formation and growth of new tumors seeded by tumor cells that have left the primary site.

Pathological angiogenesis is also associated with certain blood-borne tumors such as leukemias, and various acute or chronic neoplastic diseases of the bone marrow. It is believed that pathological angiogenesis plays a role in the bone marrow abnormalities that give rise to such leukemia-like tumors.

Pathological angiogenesis also plays a prominent role in various chronic inflammatory diseases such as inflammatory bowel diseases, psoriasis, sarcoidosis and rheumatoid arthritis. The chronic inflammation that occurs in such diseases depends on continuous formation of capillary sprouts in the diseased tissue to maintain an influx of inflammatory cells. The influx and presence of the inflammatory cells produce granulomas and thus, maintains the chronic inflammatory state.

For a general discussion of the role of angiogenesis in angiogenesis-related diseases see the following references: Moses et al., 1991, BioTechol. 9:630–633; Leek et al., 1994, J. Leuko. Biol. 56:423–435; and Beck et al., 1997, FASEB J. 11:365–373.

2.3. Angiogenic Factors and their Actions

Both normal and pathological angiogenesis apparently require action by one or more angiogenic factors. Many such factors have been identified. They include angiogenin (ANG), vascular endothelial growth factor (VEGF), basic fibroblast growth factor (bFGF), acidic fibroblast growth factor (aFGF), epidermal growth factor (EGF), tumor necrosis factor-alpha (TNF-α), tumor growth factor-alpha (TGF-α), and tumor growth factor-beta (TGF-β).

There has not been a complete elucidation of the mechanism(s) by which angiogenic factors induce the various biochemical and cellular events of angiogenesis. However, much is known regarding the action of angiogenin in inducing angiogenesis, which may at least partially model the angiogenic action of other angiogenic factors.

Angiogenin was first isolated from tumor-conditioned culture medium as a result of a search for tumor angiogenic factors (Fett et al., 1985, Biochemistry 24:5480–5486). This search was based on the hypothesis that tumors will not grow beyond a minuscule size unless they are supplied with new blood vessels to provide nutrients and facilitate gas exchange (Folkman, J., 1971, N. Engl. J. Med. 285:1182–1186). Tumors elicit the formation of new blood vessels by secreting angiogenesis factors. Angiogenin has been shown to be a potent inducer of angiogenesis (Hu et al., 1998, in *Human Cytokines, Handbook for Basic and Clinical Research*, Vol. III, ed. Aggarwal, B. B. pp. 67–91, Blackwell Sciences, Inc., Maldan, Mass.). It induces the formation of new blood vessels in the chorioallantoic membrane (CAM) of chick embryos, and in the cornea and meniscus of the knee of rabbits (Fett et al., 1985, Biochemistry 24:5480–5486, King et al., 1991, J. Bone Joint Surg. 73-B: 587–590).

Angiogenin normally circulates in human plasma at a concentration of about 250 to 360 ng/ml (Blaser et al., 1993, Eur. J. Clin. Chem. Clin. Biochem. 31: 513–516, Shimoyama et al., 1996, Cancer Res. 56:2703–2706). Plasma angiogenin may promote wound healing when it becomes extravascular, e.g., through trauma. Angiogenin mRNA and protein are elevated in tissues and cells of patients with a variety of tumors (Chopra et al., 1995, Proc. Ann. Meet. Am. Assoc. Cancer Res. 36:A516; Li et al., 1994, J. Path.

172:171–175; and Moroianu et al., 1994, Proc. Natl. Acad Sci. USA 91:1677–1681).

Structure/function studies have shown that angiogenin has a weak but characteristic ribonucleolytic activity (Shapiro et al., 1986, Biochemistry 25:3527–35328). That activity appears to be essential for its angiogenic activity (Shapiro et al., 1989, Biochemistry 28:1726–17329). Compounds that inhibit angiogenin's ribonucleolytic activity also inhibits its angiogenic activity. Many such compounds have been identified or developed. They include the C-terminal peptides of angiogenin (Rybak et al., 1989, Biochem. Biophys. Res. Comm. 162:535–543), the ribonuclease inhibitor from human placenta (Lee et al., 1988, Biochemistry 27:8545–8553, Shapiro et al., 1987, Proc. Natl. Acad Sci. USA 84:2238–2241) and, more recently, a deoxynucleotide aptamer obtained by exponential enrichment.

Angiogenin apparently must interact with endothelial cells in order to induce angiogenesis. Several such interactions have been identified. Angiogenin binds to actin (Hu et al., 1991, Proc. Natl. Acad. Sci. USA 88:2227–2231, Hu et al., 1993, Proc. Natl. Acad Sci. USA 90:1217–1221) and to a 170 kDa putative receptor (Hu et al., 1997, Proc. Natl. Acad. Sci. USA 94:2204–2209) which are expressed on the surface of endothelial cells growing in dense and sparse culture, respectively. Binding of angiogenin to endothelial cells results in activation of phospholipase C (PLC) (Bicknell et al., 1988, Proc. Natl. Acad Sci. USA 85:5961–5965), endothelial cell migration and invasion (Hu et al., 1994 Proc. Natl. Acad Sci. USA 91:12096–12100), proliferation (Hu et al., 1997, Proc. Natl. Acad. Sci. USA 94:2204–2209), and differentiation (Jimi et al., 1995, Biochem. Biophys. Res. Comm. 211:476–483). A cell binding site on angiogenin has been identified. The site is essential for angiogenic activity and yet encompasses residues not involved in the ribonucleolytic activity (Hallahan et al., 1991, Proc. Natl. Acad Sci. USA 88:2222–2226; Hallahan et al., 1992, Biochemistry, 31:8022–8029). Interference with angiogenin's interaction with its target cells inhibit its angiogenic activity. For instance, both actin and an anti-actin antibody completely abolishes angiogenin-induced angiogenesis in the CAM of chick embryos (Hu et al., 1993, Proc. Natl. Acad Sci. USA 90:1217–1221). Moreover, administration of actin prevent the growth of transplanted human tumor cells in nude mice (Olson et al., 1995, Proc. Natl. Acad. Sci. USA 92:442–446).

Translocation of angiogenin to the nucleus is apparently essential for angiogenic activity. In the interaction with endothelial cells, angiogenin is internalized and translocated to the nucleus by a process that is lysosome and microtubule independent (Moroianu et al., 1994, Proc. Natl. Acad Sci. USA 91:1677–1681; Moroianu et al., 1994, Biochem. Biophys. Res. Comm. 203:1765–1772; Li et al., 1997, Biochem. Biophys. Res. Comm. 238:305–312). Mutated angiogenins that are incapable of nuclear translocation are also incapable of inducing angiogenesis in the CAM of chick embryos (Moroianu et al., 1994, Proc. Natl. Acad Sci. USA 91:1677–1681). Such mutated angiogenins, however, have full ribonucleolytic activity and can bind to endothelial cells.

While some other angiogenic factors do not necessarily have ribonucleolytic activity, they are internalized and translocated to the nucleus (See Savion et al., 1981, J. Biol. Chem. 256:1149–1154; Bouche et al., 1987, Proc. Natl. Acad. Sci. USA 84:6770–6774; Baldin et al., 1990, EMBO J. 9:1511–1517; Sano et al., 1990, J. Cell. Biol. 110:1417–1426; Quarto et al., 1991, J. Cell. Physiol. 147:311–318). Accordingly, it has been proposed that nuclear translocation is a general pathway for those angiogenic factors that is critical to their angiogenic activity (Moroianu et al., 1994, Proc. Natl. Acad. Sci. USA 91:1677–1681; Vallee et al., 1997, CMLS Cell. Molec. Life Sci. 53:803–815).

2.4. Anti-Angiogenic Agents

The centrality of angiogenesis in the myriad of angiogenesis-related diseases has motivated searches for anti-angiogenic agents (i.e., agents that suppress or inhibit pathological angiogenesis). Such searches typically involve examining the activity of candidate agents with in vivo angiogenesis assay systems. Two well established systems for carrying out such examinations are the CAM assay and the corneal neovascularization assay. These two systems examine an agent's effect on angiogenic factor-induced capillary formation in the chorioallantoic membrane of chick embryos and the cornea of laboratory animals, respectively (Gimbrone et al., 1974, J. Natl. Cancer Inst. 52:413–427).

Many anti-angiogenic agents have been isolated or developed. They include cartilage-derived factors (Moses et al., 1990, 248:1408–1410; Oikawa et al., 1990, Cancer Lett. 51:181–186); angiostatic steroids (Folkman et al., 1983, Science 221:719–725; Crum et al., 1985, Science 230:1375–1378; Oikawa et al., 1988, Cancer Lett. 43:85–92); and angiostatic vitamin D analogs (Oikawa et al., 1989, Cancer Lett. 48:157–162; Oikawa et al., 1990, Eur. J. Pharmacol. 178:247–50) angiostatin (O'Reilly et al., 1994, Cell 79:315–328), endostatin (O'Reilly et al., 1997, Cell 88:277–285), and verostatin (Pike et al. 1998, J. Exp. Med. 88:2309–2356).

Anti-angiogenic agents that inhibit the angiogenic activity of a specific angiogenic factor, angiogenin, have also been identified or developed. They include monoclonal antibody that binds angiogenin (Fett et al., 1994, Biochem. 33:5421–5427); human placental ribonuclease inhibitor (Shapiro et al., 1987, Proc. Natl. Acad. Sci. USA 84:2238–2241); actin (Hu et al., Proc. Natl. Acad. Sci. USA 90:1217–1221); and synthetic peptides corresponding to the C-terminal region of angiogenin (Ryback et al., 1989, Biochem. Biophy. Res. Comm. 162:535–543).

Anti-angiogenic agents of microbial origin also have been identified. Such agents include anthracycline (Npzaki et al., 1993, J. Antibiot. 46:569–579), 15-deoxyspergualin (Oikawa et al., 1991, J Antibiot. 44:1033–1035), D-penicillamine (Matsubara et al., 1989, J. Clin. Invest. 83:158–167), eponemycin (Oikawa et al., 1991, Biochem. Biophys. Res. Comm. 181:1070–1076), fumagillin (Ingber et al., 1990, Nature 348:555–557), herbimycin A (Oikawa et al., 1989, J. Antibiot. 42:1202–1204), and rapamycin (Akselband et al., 1991, Transplant Proc. 23:2833–2836).

Consistent with the idea that pathological angiogenesis underlies angiogenesis-related diseases, many anti-angiogenic agents have been demonstrated to have beneficial therapeutic activity against such diseases. Various types of tumors have been shown to be susceptible to treatments with anti-angiogenic agents. For example, several anti-angiogenin monoclonal antibodies exhibit significant anti-tumor activity in preventing or delaying the appearance of several different types of tumor xenografts in athymic mice (Olsen et al., 1994, Cancer Res. 54:4576–4579; Olson et al., 1995, Proc. Natl. Acad. Sci. USA 92:442–446). Actin, an angiogenin antagonist, has been shown to inhibit the establishment of various tumor xenografts in athymic mice (Olson et al., 1995, Proc. Natl. Acad. Sci. USA 92:442–446). Eponemycin inhibits the growth of B 16 melanomas (Sugawara et al., 1990, J Antibiot. 43:8–18). 22-oxa-1 α,25-dihydroxyvitamin $D_2$, a potent angiogenesis inhibitor, has been shown to suppress the growth of autochthonous mammary tumors in rats (Oikawa et al., 1991, Anti-Cancer Drugs 2:475–480). AGM-1470, a synthetic analog of fumagillin, has been shown to inhibit the growth of various types of transplanted tumors in mice (Ingber et al., 1990, Nature 348:555–557).

D-penicillamine, in the presence of copper, suppresses angiogenesis. It has been proposed that that activity accounts for the compound's efficacy in suppressing the inflammatory symptoms of rheumatoid synovitis, which involve pathological proliferation of small blood vessel in the synovium tissue (Matsubara et al., 1989, J. Clin. Invest. 83:158–167).

2.5. Neomycin

Neomycin is an aminoglycoside antibiotic derived from *Streptomyces fradiae*. It is bactericidal for many gram-negative and gram-positive organisms. It is in clinical use for oral treatment of enteral infections, to reduce microbe numbers in the colon prior to colon surgery, and orally or in enema form to reduce ammonia-producing bacteria in the treatment of hepatic encephalopathy. Absorption of neomycin from the intestinal tract is relatively poor. The usual oral dose is 4 to 8 Gm in divided doses per day. Neomycin is also administered intramuscularly, using a daily dose of 1 to 6 Gm. Damage to the kidney and the eighth nerve occurs in a significant number of patients when neomycin is given parenterally at a higher dose.

Citation or identification of any reference herein shall not be construed as an admission that such reference is available as prior art to the present invention.

3. SUMMARY OF THE INVENTION

The present invention provides a novel method for treating subjects having an angiogenesis-related disease. The method comprises administering to such subjects neomycin or an analogue thereof In a preferred embodiment, neomycin is administered to a subject having an angiogenesis-related disease. In other embodiments, neomycin or an analogue thereof is administered with other anti-angiogenesis agent(s) to such subjects. In additional embodiments, neomycin or an analogue thereof is administered with an anti-cancer agent to treat a subject having an angiogenesis-related disease which is a cancer.

Angiogenesis-related diseases involve excessive, inappropriate or undesired angiogenesis. Without intending to limit the present invention to any particular theory, it is believed that the disease state of angiogenesis-related diseases requires continuing action by one or more angiogenic factors, and such action requires nuclear translocation of the involved angiogenic factor(s). The present invention is based on the surprising discovery that neomycin and Analogues can inhibit nuclear translocation of angiogenic factors and have anti-angiogenic activity (i.e., inhibit angiogenic factor-induced angiogenesis).

The present invention is illustrated by way of examples that demonstrate the efficacy of neomycin in inhibiting the nuclear translocation of angiogenic factors, suppressing angiogenic factor-induced proliferation of endothelial cells, and inhibiting in vivo angiogenesis induced by certain angiogenic factors.

3.1. Definitions

In order to provide a clear and consistent understanding of the specification and claims, including the scope to be given to a term, the following definitions are given to various terms and abbreviations used herein.

| | |
|---|---|
| aFGF | acidic fibroblast growth factor |
| Analogue(s) | the term "Analogue(s)" (capitalized) is used herein to mean analogue(s) of neomycin as defined in Section 5.1, infra. |
| anti-angiogenic | the ability to inhibit angiogenesis, preferably angiogenic factor-induced angiogenesis |
| bFGF | basic fibroblast growth factor |
| CAM | chorioallantoic membrane |
| cancer | a disease characterized by the formation of solid or blood borne tumors |
| EC | endothelial cell |
| EGF | epidermal growth factor |
| FBS | fetal bovine serum |
| HE-SFM | human endothelial serum-free medium |
| HUVE | human umbilical vein endothelial |
| IP | inositol phosphate |
| PBS | phosphate-buffered saline |
| PLC | phospholipase C |
| TGF-α | tumor growth factor-alpha |
| TGF-β | tumor growth factor-beta |
| TNF-α | tumor necrosis factor-alpha |
| VEGF | vascular endothelial growth factor |

4. BRIEF DESCRIPTION OF THE FIGURES

FIG. 1. Neomycin inhibits nuclear translocation of $^{125}$I-angiogenin in HUVE cells. HUVE cells, cultured at 50,000 cells per 35 mm dish, were treated with neomycin at the concentration indicated. $^{125}$I-angiogenin was added to a final concentration of 1 µg/ml and incubated at 37° C. for 30 min. Nuclear fractions were isolated and radioactivities were determined. Data shown are relative percentage to the control and are from the mean of duplicate samples.

Figure 2:
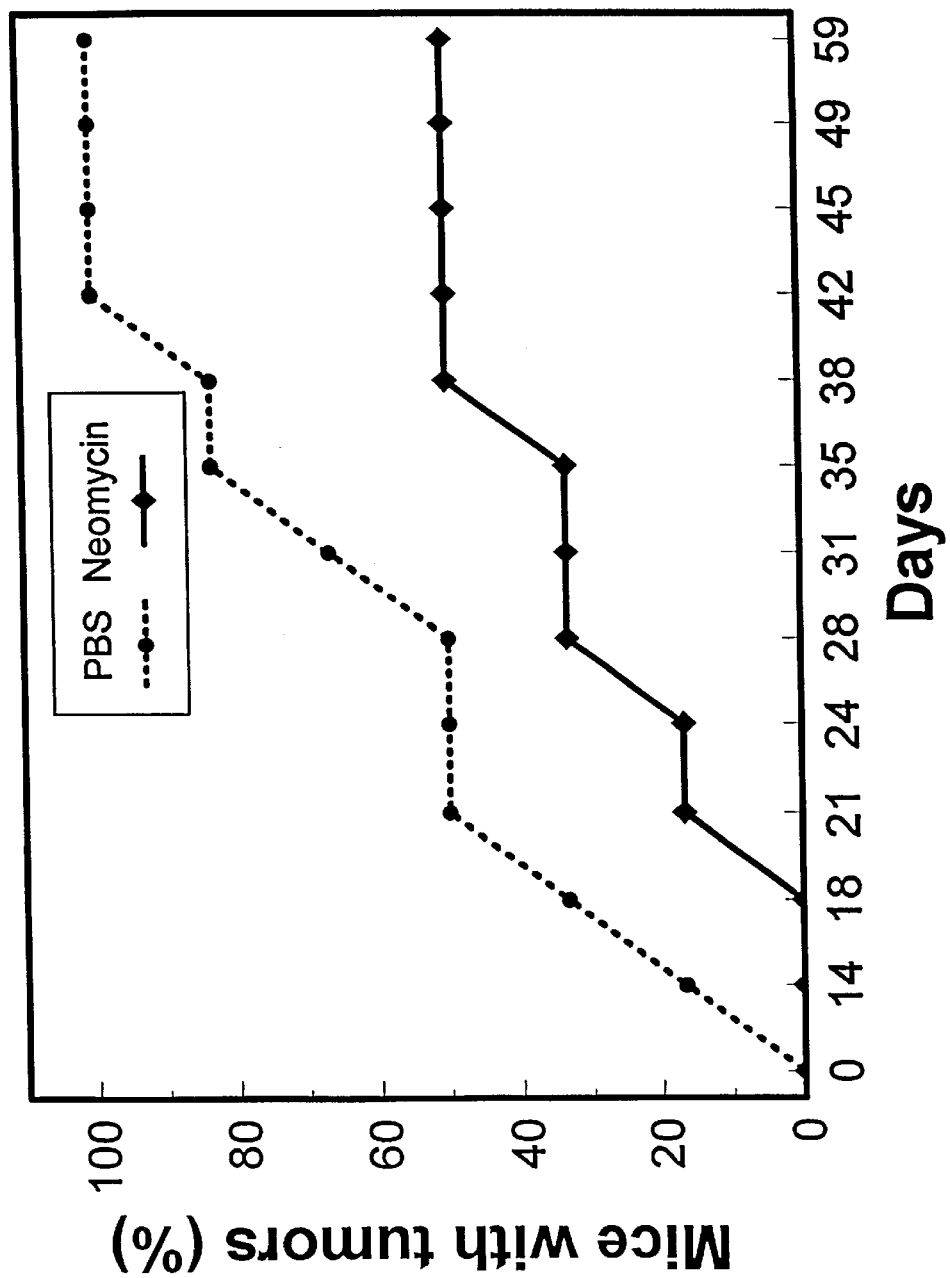

FIG. 2. Neomycin inhibits angiogenin-induced proliferation of HUVE cells. HUVE cells were cultured at a density of 4,000 cells per cm$^2$ and were stimulated with 1 µg/ml angiogenin in the absence or presence of neomycin at the concentration indicated at 37° C. for 48 hr. Percentage increase of cell number stimulated by angiogenin in each neomycin concentration over the corresponding control was calculated from the mean of cell numbers of duplicate samples and was compared with that in the absence of neomycin, which was defined as 100% proliferative activity.

Figure 3:
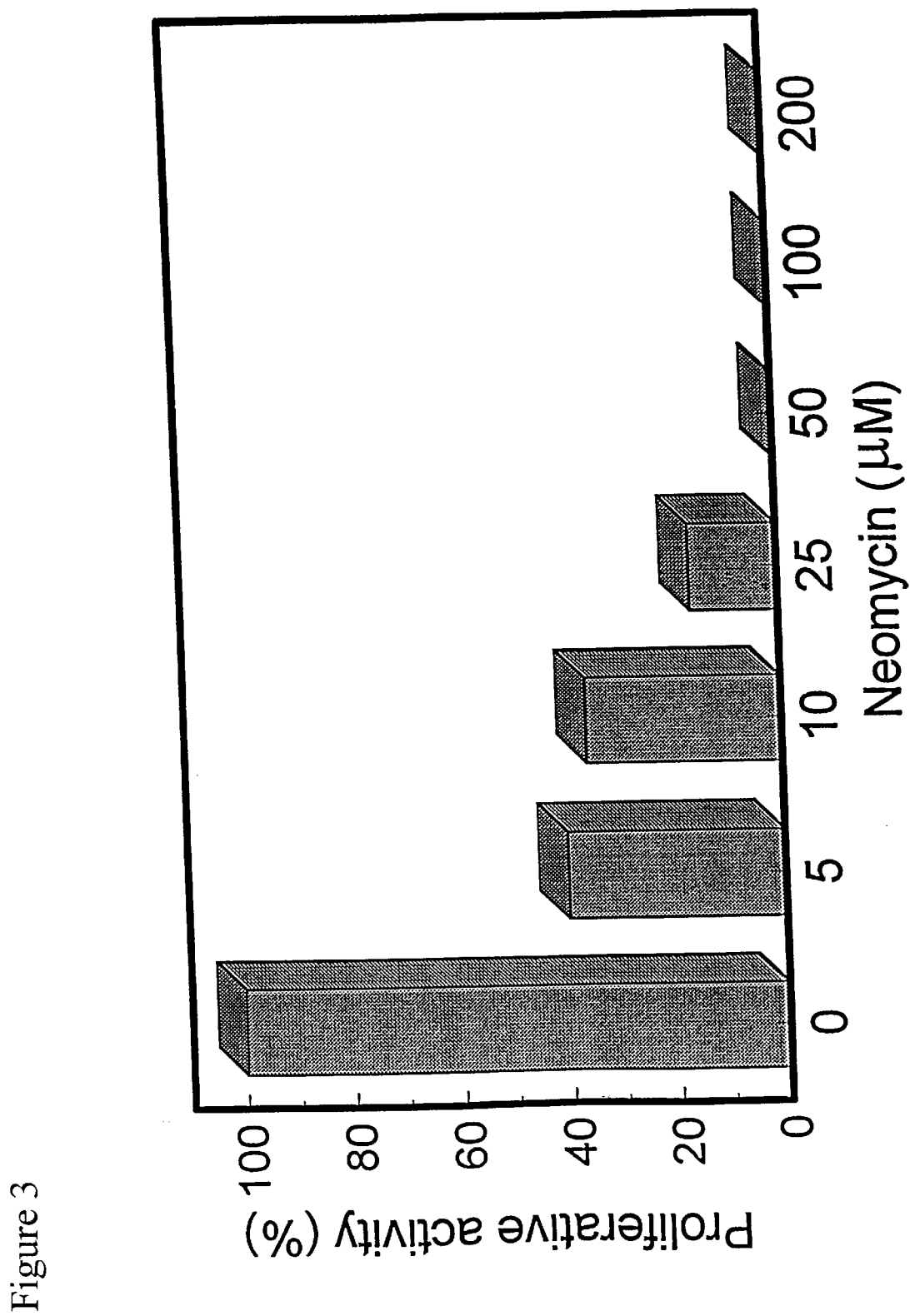

FIG. 3. Neomycin inhibits growth of PC-3 human prostate tumor cells in athymic mice. PC-3 human prostate tumor cells were harvested by trypsinization and viability was determined by trypan blue dye exclusion method. The cells, 1×10$^4$, were mixed with 33 µl of Matrigel and either control or neomycin at a dose of 20 mg/kg body weight. The preparation containing the cells, Matrigel and either control or neomycin was then diluted with PBS to a total volume of 100 µl, which was injected subcutaneously at a site behind the left shoulder. Subsequent injection of PBS (dotted line) or neomycin (solid line) at a dose of 20 mg/kg body weight was administered subcutaneously 6 times per week for 20 days and 4 times per week for another 30 days.

Figure 4:
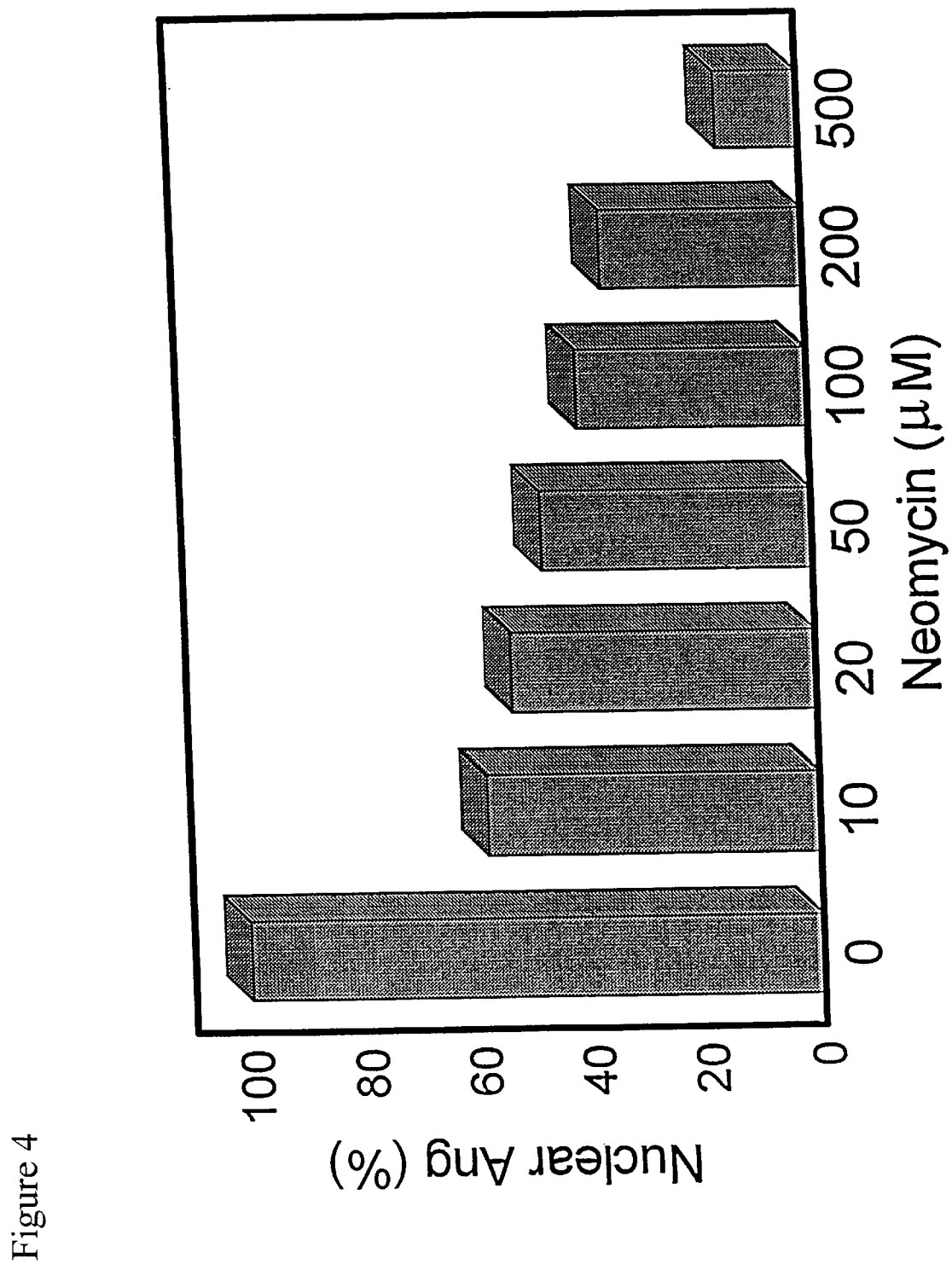

FIG. 4. Neomycin inhibits growth of MDA-MB-435 human breast tumor cells in athymic mice. MDA-MB-435 human breast tumor cells were harvested by trypsinization and viability was determined by trypan blue dye exclusion method. A total of 1×10$^4$ cells in 20 µl was injected into the mammary fat pad of the mice. Daily treatment with PBS (dotted line) or neomycin (solid line) at a dose of 60 mg/kg body weight was administered intraperitoneally for 20 days followed by 4 times per week for another 42 days.

5. DETAILED DESCRIPTION OF THE INVENTION

The present invention is directed to a method for treating or preventing angiogenesis-related diseases by administering neomycin or an Analogue. Angiogenesis-related diseases are associated with or supported by pathological angiogenesis (i.e., inappropriate, excessive or undesired formation of blood vessels), which apparently is induced by various angiogenic factors. The present invention is also directed to pharmaceutical compositions comprising neomycin or an Analogue and, optionally, another anti-angiogenic agent or an anti-cancer agent. The present invention is further directed to a method for screening neomycin analogues having anti-angiogenic activity.

According to the present invention, the aminoglycoside antibiotic neomycin and analogues thereof inhibit two apparently essential steps required for induction of angiogenesis by most, if not all, angiogenic factors: induction of proliferation of endothelial cells and nuclear translocation of the. angiogenic factor. More significantly, neomycin and analogues thereof inhibit pathological angiogenesis associated with many disease states.

In the examples provided infra, neomycin inhibited angiogenin-induced EC proliferation and angiogenin nuclear translocation with an $IC_{50}$ of about 10 μM and 50 μM, respectively. Neomycin completely abolished angiogenin-induced angiogenesis in the chorioallantoic membrane (CAM) of chick embryos at a dosage of about 20 ng per embryo.

Neomycin also inhibited the actions of other angiogenic factors. It inhibited the nuclear translocation of angiogenic factors bFGF, aFGF, and EGF in endothelial cells. Proliferation of endothelial cells induced by these factors were inhibited by neomycin with an $IC_{50}$ of about 100 μM. Neomycin inhibited bFGF-, aFGF- and EGF-induced angiogenesis in the CAM of chick embryos at a dosage of about 200 ng per embryo.

Further, whereas neomycin inhibited VEGF-induced proliferation of endothelial cells, it did not significantly reduce the angiogenic activity of VEGF on the CAM of chick embryos at a dosage as high as 900 ng per embryo. Since VEGF is a pleiotropic angiogenic factor implicated in both normal and neoplastic angiogenesis, whereas other angiogenic factors may be more involved in pathological angiogenesis, these results suggest that neomycin may be used as an anti-angiogenic agent that selectively inhibits the pathological angiogenesis associated with many diseases, but not normal angiogenesis.

Additionally, neomycin caused no cytotoxicity in cultured human endothelial cells up to a concentration of about 200 μM. Similarly, neomycin caused no necrosis or any other visible adverse effect on the chick embryo at the various dosage applied. Thus, therapeutic administration of neomycin or Analogue can be used to beneficially ameliorate the symptoms of angiogenesis-related diseases or suppress conditions that are required for developing or continuing such diseases.

5.1. Neomycin and Analogues

The present invention contemplates the use of neomycin or an analogue thereof in the method of the invention to treat or prevent an angiogenesis-related disease. As used herein, the term "neomycin" refers to the antibiotic complex composed of neomycins A, B and C (the complex is known by various common names such as Mycifradin, Myacyne, Fradiomycin, Neomin, Neolate, Neomas, Nivemycin, Pimavecort, Vonamycin Powder V). In a preferred embodiment, neomycin is used in the method of the invention to treat or prevent angiogenesis-related diseases.

As used herein, the term "neomycin analogue" refers to: (a) any individual component of the neomycin complex, i.e., neomycin A (also known as Neamine), or neomycin B (also known as Framycetin, Enterfram, Framygen, Soframycin, Actilin, and antibiotique EF 185), or neomycin C; or (b) a complex comprising neomycin A, neomycin B, or neomycin C; (c) an aminoglycoside having a structure substantially similar to that of neomycin A or B or C (hereinafter "structural analogue of neomycin"); or (d) a chemical or biological breakdown product of neomycin A or B or C, such as neobiosamine C, which is released upon hydrolysis of neomycin C; (e) a derivative of neomycin A or B or C, such as neomycin LP-B or neomycin LP-C; or (f) a naturally-occurring precursor to neomycin A or B or C.

As used herein, a structural analogue of neomycin is a substituted-2-deoxystreptamine (2-DOS) linked to two to four pentose or hexose sugars. Such structural analogues include, but are not limited to, the neomycin, paromomycin or lividomycin aminoglycoside family. Preferably, a structural analogue of neomycin has a glucosyl residue attached to the 4 position of the 2-DOS moiety, which glucosyl residue comprises an amino group at each of the 2 and 6 positions. Such preferred structural analogues of neomycin include, but are not limited to, nebramine, gentamine $C_1$, gentamine $C_2$, gentamine $C_{1a}$, ribostamycin, xylostasin. For a discussion of the structure and biological activity of neomycin family of aminoglycosides and related aminoglycosides see *Aminoglycoside Antibiotics*, ed. Umezawa, Spriner, Berlin, 1982, and Rhinehart, K. L., *The Neomycins and Related Antibiotics*, Wiley & Sons, New York, 1961. As contemplated by the present invention, neomycin analogues may or may not have antimicrobial activity.

Neomycin analogues that may be used in the method of the invention preferably have structures that are substantially similar to that of neomycin B or C. As used herein, such substantially similar analogues are 4,5-disubstituted-2-deoxystreptamines comprising a 2-DOS and a 2,6-diamino-2-6-dideoxy-D-glucose (i.e., neosamine C) attached to the 4 position of 2-DOS.

Neomycin analogues that may be used in the method of the invention also can be selected based on the following biological criteria. In one embodiment, the neomycin analogue selected for use in the method of the invention (the "selected neomycin analogue") is one which inhibits (a) the nuclear translocation of an angiogenic factor, or (b) the ribonucleolytic activity of angiogenin. Neomycin analogues can be tested for such activity according to assays such as those described in Sections 6.1.1.4, 6.1.1.6 and 6.2.1, infra, or known in the art.

In yet another embodiment, the selected neomycin analogue is one which inhibits the activity of phospholipase C. Neomycin analogues can be tested for such activity according to known assays (see Somjen et al., 1997, J. Cell. Biochem. 65:53–66; Hildebrandt et al., 1997, Bri. J. Phar. 120:841–850).

In a preferred embodiment, the selected neomycin analogue is any of the following: neomycin A, neomycin B or neomycin C or a complex comprising neomycin A, neomycin B, or neomycin C.

In an additional preferred embodiment, the selected neomycin analogue is one which reduces or inhibits inflammatory angiogenesis. Neomycin analogues can be tested for such activity according to assays such as the murine air-pouch granuloma model of chronic inflammation (see Kimura et al., 1985, J. Pharnacobio-Dyn. 8:393–400; Colville-Nash et al., 1995, J. Pharm. Exp. Ther. 274:1463–142; and International Publ. No. WO 07/35567).

In a further preferred embodiment, the selected neomycin analogue is one which inhibits angiogenic factor-induced proliferation of endothelial cells. Such activity can be determined using cell proliferation assays such as those that are described in Sections 6.1.1.5 and 6.3.1, infra, or known in the art.

In another preferred embodiment, the selected neomycin analogue is one which inhibits angiogenic factor-induced angiogenesis. In yet another preferred embodiment, the selected neomycin analogue is one which inhibits angiogenesis induced by an angiogenic factor other than VEGF. Neomycin analogues can be tested for their activity in inhibiting angiogenic factor-induced angiogenesis using the CAM assay, as described in Section 6.1.1.7, infra, the corneal neovascularization assay (Gimbrone et al., 1974, J. Natl. Cancer Inst. 52:413–427), or other similar assays known in the art.

According to the present invention, angiogenic factors include, but are not limited to, angiogenin (ANG), vascular endothelial growth factor (VEGF), basic fibroblast growth factor (bFGF), acidic fibroblast growth factor (aFGF), epidermal growth factor (EGF), tumor necrosis factor-alpha (TNF-α), tumor growth factor-alpha (TGF-α), and tumor growth factor-beta (TGF-β), platelet-derived growth factor (PDGF), platelet-derived endothelial cell growth fqactor (PD-ECGF), placental growth factor (PIGF), hepatocyte growth fctor (HGF), platelet activating factor (PAF), insulin-like growth factor (IGF), interleukin-8 (IL-8), and granulocyte-colony stimulating factor (GCSF).

5.1.1. Methods for Selecting Neomycin Analogues

The present invention provides methods for selecting neomycin analogues that can used in the therapeutic method of the invention. The contemplated selection methods include all of the assays referenced in Section 5.1, supra.

In a preferred embodiment, the selection method is based on an Analogue's activity for inhibiting nuclear translocation of an angiogenic factor. Such method may comprise (a) incubating endothelial cells with a neomycin analogue and a labeled-angiogenic factor; and (b) determining the amount of labeled-angiogenic factor present in the nuclei of such cells. Alternatively, the method may comprise (a) incubating endothelial cells in a growth medium with a neomycin analogue, (b) incubating the neomycin analogue-treated endothelial cells with a labeled-angiogenic factor; and (c) determining the amount of labeled-angiogenic factor present in the nuclei of the endothelial cells. The label attached to the angiogenic factor may be any known in the art including, but not limited to, a radioactive molecule or atom, a fluorescent molecule, and a phosphorescent molecule. In a specific embodiment, the method comprises (a) incubating a first culture of endothelial cells with the neomycin analogue and an angiogenic factor in a growth medium, and incubating a second culture of endothelial cells with the angiogenic factor in the growth medium lacking the neomycin analogue, wherein the angiogenic factor is labeled; (b) determining the amounts of angiogenic factor present in the nuclei of cells in the first and the second cultures; and (c) selecting for use in treating the angiogenesis-related disease, the neomycin analogue that inhibits nuclear translocation of the angiogenic factor in cells of the first culture by at least 10% of the amount of the angiogenic factor translocated to the nuclei of the cells in the second culture. In another embodiment, the method comprises (a) incubating a first culture of endothelial cells with the neomycin analogue in a growth medium, and incubating a second culture of endothelial cells in a growth medium lacking the neomycin analogue; (b) incubating the first and the second cultures with an angiogenic factor in the growth medium, wherein the angiogenic factor is labeled; (c) determining the amount of angiogenic factor present in the nuclei of cells in the first and the second cultures; and (d) selecting for use in treating the angiogenesis-related disease, the neomycin analogue that inhibits nuclear translocation of the angiogenic factor in the cells of the first culture by at least 10% of the amount of nuclear translocation of the angiogenic factor in the cells of the second culture. In preferred embodiments, a neomycin analogue is selected for use in the therapeutic method of the invention if it inhibits nuclear translocation of the angiogenic factor by at least 25% of the level of the angiogenic factor translocated to the nuclei of the control culture (i.e., cells that were not treated with the neomycin analogue). In a most preferred embodiment, the selected neomycin analogue inhibits nuclear translocation of the angiogenic factor by at least 50% of the level of the angiogenic factor translocated to the nuclei of the control culture.

In another preferred embodiment, the selection method is based on an Analogue's activity for inhibiting the proliferation of endothelial cells induced by an angiogenic factor. Such method may comprise (a) incubating endothelial cells in a neomycin analogue containing growth medium with or without an angiogenic factor; (b) determining the cell numbers of the cultures with or without the angiogenic factor; and (c) comparing the percentage decrease or increase in cell number in the culture treated with the angiogenic factor and the Analogue over that of the culture treated with just the Analogue with the percentage decrease or increase in cell number in a culture treated with the same concentration of angiogenic factor over that of a culture not treated with the angiogenic factor. In a specific embodiment, the method comprises (a) incubating a first culture of endothelial cells with the neomycin analogue and an angiogenic factor in a growth medium, incubating a second culture of endothelial cells with the neomycin analogue in the growth medium lacking the angiogenic factor, incubating a third culture of endothelial cells with the angiogenic factor in the growth medium lacking the neomycin analogue, incubating a fourth culture of endothelial cells in the growth medium lacking the neomycin analogue and the angiogenic factor; (b) determining the cell numbers of the first, the second, the third and the fourth cultures; and (c) selecting for use in treating the angiogenesis-related disease, the neomycin analogue that reduces the increase in the cell number in the second culture over the cell number in the first culture to less than about 75% of the increase in cell number of the third culture over the cell number of the fourth culture. In a preferred embodiment, a neomycin analogue is selected for use in the therapeutic method of the invention if it inhibits the proliferation of endothelial cells to less than 50% of the level of angiogenic factor-induced proliferation in the control cultures. In a most preferred embodiment, the selected neomycin analogue completely inhibits the proliferation of endothelial cells induced by the angiogenic factor.

The endothelial cells used in the above-described assays may be any known in the art, preferably HUVE. The growth medium used such assays may also be any known in the art, preferably, HE-SFM.

In a more preferred embodiment, the selection method is based on an Analogue's activity for inhibiting angiogenesis induced by an angiogenic factor. Such method may comprises the CAM assay as known in the art (see, e.g., Knighton et al., 1977, Br. J. Cancer 35:347–356; Fett et al., 1985, Biochemistry 24:5480–5486) or the corneal neovascularization assay as known in the art (see, e.g., Gimbrone et al., 1974, J. Natl. Cancer Inst. 52:413–427). The CAM assay may comprise: (a) applying an neomycin analogue to CAM of chick embryos treated with or without an angiogenic factor; (b) incubating the treated chick embryos; (b) determining the number of embryos having an angiogenic response (i.e., formation of blood vessels); and (d) comparing the percentage decrease or increase of angiogenic response in the embryos treated with the angiogenic factor and the analogue over the angiogenic response in the embryos treated with just the analogue, with the percentage decrease or increase in angiogenic response in embryos treated with the same concentration of angiogenic factor over that of embryos not treated with the angiogenic factor. In a specific embodiment, the CAM assay comprises (a) contacting the chorioallantoic membrane of a first group of chick embryos with the neomycin analogue and an angiogenic factor, contacting the chorioallantoic membrane of a second group of chick embryos with the neomycin analogue but not the angiogenic factor, contacting the chorioallantoic membrane of a third group of chick embryos with the angiogenic factor but not the neomycin analogue, and contacting the chorioallantoic membrane of a fourth group of chick embryos with a solution lacking the neomycin analogue and the antigenic factor; (b) incubating the first, the second, the third and the fourth groups of chick embryos; (c) determining the numbers of embryos having an angiogenic response in the first, the second, the third and the fourth groups of embryos; and (d) selecting for use in treating the angiogenesis-related disease, the neomycin analogue that reduces the increase in the number of embryos exhibiting an angiogenic response in the second group of embryos over the number of embryos exhibiting an angiogenic response in the first group of embryos to less than about 75% of the increase in the number of embryos exhibiting an angiogenic response in the third group of embryos over the number of embryos exhibiting an angiogenic response in the fourth group of embryos. In a more preferred embodiment, the selected neomycin analogue inhibits angiogenic factor-induced angiogenesis to less than 50% of the level of angiogenic factor-induced angiogenesis in the control groups of embryos (i.e., those contacted with or without the angiogenic factor only). In a more preferred embodiment, the selected neomycin analogue inhibits angiogenic factor-induced angiogenesis to less than 25% of the level of angiogenic factor-induced angiogenesis in the control groups of embryos.

5.2. Therapeutic Methods and Compositions

The present invention is directed to a method for treating a subject having an angiogenesis-related disease which comprises administering to the subject a therapeutic amount of neomycin or analogue thereof sufficient to (a) inhibit the pathological angiogenesis associated with the disease, or (b) ameliorate or eliminate any other pathological symptoms of the disease. As used herein, the term "inhibit" means suppress, arrest, prevent, reduce or retard, and the term "pathological angiogenesis" refers to the inappropriate, excessive or undesired formation of blood vessels that is associated with an angiogenesis-related disease or that supports continuation of the disease.

The subject treated by the methods of the invention is an animal, preferably a mammal, and more preferably a human. In one embodiment, the present invention is directed to treatment or prevention of angiogenesis-related diseases of humans. In another embodiment, the present invention is directed to treatment or prevention of angiogenesis-related diseases of domestic animals, such as murine, rodent, feline or canine subjects, and farm animals, such as but not limited to bovine, equine and porcine subjects.

The present invention provides pharmaceutical compositions which comprise neomycin or an analogue thereof, as described in Section 5.1, supra,. Such compositions may optionally (i.e., additionally) comprise other therapeutic agents including, but not limited to, other anti-angiogenic agents and/or anti-neoplastic agents.

According to the invention, such other anti-angiogenic agents include, but are not limited to, thalidomide (D'Amato et al. 1994, Proc. Natl. Acad. Sci. USA 91:4082–4085; U.S. Pat. No. 5,712,291); angiostatic steroids such as 2-methoxyestradiol (D'Amato et al. 1994, Proc. Natl. Acad. Sci. USA 91:3964–3968; see also Folkman et al., 1983, Science 221:719–725; Crum et al., 1985, Science 230:1375–1378; Oikawa et al., 1988, Cancer Lett. 43:85–92); endostatin (O'Reilly et al., 1997, Cell 88:277–285); angiostatin (O'Reilly et al., 1994, Cell 79:315–328; U.S. Pat. No. 5,639,725); platelet factor-4 (Maione et al., 1990, Science 247:77–79); anti-angiogenic sulfated polysaccharides such as dextran sulfate and beta-1,3-glucan sulfate (U.S. Pat. No. 5,135,9200; cytokines such as interferon-alpha (Folkman 1996, Scientific American 275:150) and interleukin-12 (Folkman 1996, Scientific American 275:150); anti-angiogenic cartilage-derived inhibitors (Moses et al., 1990, Science 248:1408–1410; Oikawa et al., 1990, Cancer Lett. 51:181–186); angiostatic vitamin D analogs such as 22-oxa-1 α,25-dihydroxyvitamin $D_2$ (Oikawa et al., 1989, Cancer Lett. 48:157–162; Oikawa et al., 1990, Eur. J. Pharmacol. 178:247–50); antibodies that bind angiogenin, such as monoclonal antibodies 26-2F and 36 U (Fett et al., 1994, Biochemistry 33:5421–5427; Olson et al., 1995, Proc. Natl. Acad. Sci. USA 92:442–446) and chimeric or humanized anti-angiogenin antibodies (Piccoli et al., 1998, Proc. Natl. Acad. Sci. USA 95:4579–4583); peptide that interferes with angiogenin interaction with its receptor, such as NH2-Val-Phe-Ser-Val-Arg-Val-Ser-Ile-Leu-Val-Phe-COOH (SEQ ID NO: 1), $NH_2$-Leu-Leu-Phe-Leu-Pro-Leu-Gly-Val-Ser-Leu-Leu-Asp-Ser-COOH (SEQ ID NO: 2), $NH_2$-Ala-Gln-Leu-Ala-Gly-Glu-Cys-Arg-Glu-Asn-Val-Cys-Met-Gly-Ile-Glu-Gly-Arg-COOH (SEQ ID NO: 3) and derivatives thereof (Gho et al., 1997, Cancer Res. 57:3733–3440; Gho et al., 1997, J. Biol. Chem. 272:24294–24299); human placental ribonuclease inhibitor (Shapiro et al., 1987, Proc. Natl. Acad. Sci. USA 84:2238–2241); actin and fragments thereof that interferes with angiogenin interaction with its receptor, such as $NH_2$-Tyr-Ser-Val-Trp-Ile-Gly-Gly-Ser-Ile-Leu-Ala-Ser-Leu-Ser-Thr-Phe-Gln-Gln-Met-Trp-Ile-Ser-Lys-COOH (SEQ ID NO: 4) and derivatives thereof (Hu et al., Proc. Natl. Acad. Sci. USA 90:1217–1221); nucleotides that inhibit the ribonucleolytic activity of angiogenin, such as 5'-CGGACGAATGCTTTGATGTTGTGCTGGACCAG CGTTCATTCTCA-3'(SEQ ID NO: 5) and derivatives thereof; anthracycline; 15-deoxyspergualin; D-penicillamine; eponemycin; fumagillin and its derivatives such as AGM-1470 (Ingber et al., 1990, Nature 348:555–557; U.S. Pat. Nos. 5,135,919 and 5,698,586); herbimycin A; rapamycin; CAI (Folkman J., 1996, Sci. Amer. 275:150); CM101 (Folkman J., 1996, Sci. Amer. 275:150); and marimastat (Folkman J., 1996, Sci. Amer. 275:150).

The pharmaceutical compositions of the invention may optionally comprise one or more anti-neoplastic agents, which include, but are not limited to, alkaloids such as docetaxel, etoposide, trontecan, paclitaxel, teniposide, topotecan, vinblastine, vincristine, and vindesine; alkylating agents such as busulfan, improsulfan, piposulfan, aziridines, benzodepa, carboquone, meturedepa, uredepa, altretamine, triethylenemelamine, triethylenephosphoramide, triethylenethiophosphoramide, chlorambucil, chloraphazine, cyclophosphamide, estramustine, ifosfamide, mechlorethamine, mechlorethamine oxide hydrochloride, melphalan, novembichin, perfosfamide, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, temozolomide; antibiotics and analogues such as aclacinomycinsa actinomycin $F_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycins, peplomycin, pirarubicin, plicamycin, porfiromycin, puromycin, streptonigrin, streptozocin, tubercidin, zinostatin, zorubicin; antimetabolites such as denopterin, edatrexate, methotrexate, piritrexim, pteropterin, Tomudex®, trimetrexate, cladribine, fludarabine, 6-mercaptopurine, thiamiprine, thioguanine, ancitabine, azacitidine, 6-azauridine, carnofur, cytarabine, doxifluridine, emitefur, enocitabune, floxuridine, fluorouracil, gemcitabine, tegafur; L-Asparaginase; immunomodulators such as interferon-α, interferon-β, interferon-γ, interleukin-2, lentinan, propagermanium, PSK, roquinimex, sizofican, ubenimex; platimum complexes such as carboplatin, cisplatin, miboplatin, oxaliplatin; aceglarone; amsacrine; bisantrene; defosfamide; demecolcine; diaziquone; eflornithine; elliptinium acetate; etoglucid; fenretinide; gallium nitrate; hydroxyurea; lonidamine; miltefosine; mitoguazone; mitoxantrone; mopidamol; nitracine; pentostain; phenamet; podophyllinic acid 2-ethyl-hydrazide; procabazine; razoxane; sobuzoxane; spirogermanium; tenuzonic acid; triaziquone; 2,2',2"trichlorotriethylamine; urethan; antineoplastic hormone or analogues such as calusterone, dromostanolone, epitiostanol, mepitiostane, testolacone, aminoglutethimide, mitotane, trilostane, bicalutamide, flutamide, nilutamide, droloxifene, tamoxifen, toremifene, aminoglutethimide, anastrozole, fadrozole, formestane, letrozole, fosfestrol, hexestrol, polyestradiol phosphate, buserelin, goserelin, leuprolide, triptorelin, chlormadinone acetate, medroxyprogesterone, megestrol acetate, melengestrol; porfimer sodium; batimastar; and folinic acid. For a description of these and other antineoplastic agents that may comprise the pharmaceutical composition of the invention see *The Merck Index*, 12th ed. pp. THER 13–14. Compositions comprising an anti-neoplastic agent are particularly useful for treating angiogenesis-related diseases that are cancers (i.e., solid or blood-borne tumors).

According to the present invention, compositions of the invention can be administered by any of the routes used conventionally used for drug administration. Such routes include, but are not limited to, orally, topically, parenterally and by inhalation. Parenteral delivery may be intraperitoneal, intravenous, perioral, subcutaneous, intramuscular, intraarterial, etc.

Compositions of the invention may be administered in conventional dosage forms prepared by combining with standard pharmaceutically acceptable carriers according to procedures known in the art. Such combinations may involve procedures such as mixing, granulating, compressing and dissolving the appropriate ingredients.

The form and nature of the pharmaceutically acceptable carrier is controlled by the amounts the active ingredient with which it is combined, the route of the administration and other well-known variables. As used herein, the term "carrier" refers to diluents, excipients and the like for use in preparing admixtures of a pharmaceutical composition. The term "pharmaceutically acceptable" means approved by a regulatory agency of the Federal or a state government or listed in the U.S. Pharmacopeia or other generally recognized pharmacopeia for use in animals, and more particularly in humans. Such pharmaceutically acceptable carriers or diluents and methods for preparing are well known in the art (see, e.g., *Remington's Pharmaceutical Sciences,* Meade Publishing Col., Easton, Pa., latest edition; the Handbook of Pharmaceutical Excipients, APhA publications, 1986).

Pharmaceutically acceptable carriers may be, for example, a liquid or solid. Liquid carriers include, but are not limited, to water, saline, buffered saline, dextrose solution, preferably such physiologically compatible buffers as Hank's or Ringer's solution, physiological saline, a mixture consisting of saline and glucose, and heparinized sodium-citrate-citric acid-dextrose solution and the like, preferably in sterile form. Exemplary solid carrier include agar, acacia, gelatin, lactose, magnesium stearate, pectin, talc and like.

Compositions of the invention can be administered orally. For such administrations, the pharmaceutical composition may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets, capsules or pellets prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

For buccal administration, the compositions may take the form of tablets, troche or lozenge formulated in conventional manner.

Compositions, e.g., for oral or buccal administration, may be suitably formulated to give controlled release of the active compound. Such formulations may include one or more sustained-release agents known in the art, such as glyceryl mono-stearate, glyceryl distearate and wax.

Compositions of the invention may be applied topically. Such administrations includes applying the compositions externally to the epidermis, the mouth cavity, and the instillation into the eye, ear and nose, such that the neomycin or Analogue does not significantly enter the blood stream. This contrasts with systemic administration achieved by oral, intravenous, intraperitoneal and intramuscular delivery.

Compositions for use in topical administration include, e.g., liquid or gel preparations suitable for penetration through the skin such as creams, liniments, lotions, ointments or pastes, and drops suitable for delivery to the eye, ear or nose.

According to the invention, creams, drops, liniments, lotions, ointments and pastes are liquid or semi-solid compositions for external application. Such compositions may be prepared by mixing the active ingredient(s) in powdered form, alone or in solution or suspension in an aqueous or non-aqueous fluid with a greasy or non-greasy base. The base may comprise complex hydrocarbons such as glycerol, various forms of paraffin, beeswax; a mucilage; a mineral or edible oil or fatty acids; or a macrogel. Such compositions may additionally comprise suitable surface active agents such as surfactants, and suspending agents such as agar, vegetable gums, cellulose derivatives, and other ingredients such as preservatives, antioxidants, etc.

According to the invention, lotions and drops include those suitable for application to the eye or skin. Eye lotions and drops may comprise a sterile aqueous solution, oily solutions or suspensions maybe prepared by dissolving the active ingredient(s) in a suitable aqueous solution. Such solutions may optionally contain a suitable bactericide, fungicide, preservative, and surfactant. Lotions or liniments for applying to the skin may also comprise drying agents such as alcohol and/or a moisturizer such as glycerol, an oil or fatty acid.

Compositions of the invention also can be administered nasally or by inhalation. For nasal or inhalation administration, the compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Compositions of the invention may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

Compositions of the invention comprise neomycin or Analogue, which may be in the form of a free base or acid, or a pharmaceutically acceptable salt thereof. Such salts are well known in the art. They include, but are not limited to, salts of inorganic and organic acids such as hydrochloric acid, hydrobromic acid, phosphoric acid, sulfuric acid, acetic acid, citric acid, fumaric acid, lactic acid, maleic acid, oxalic acid, phenylacetic acid, salicylic acid, succinic acid, and tartaric acid.

In preferred embodiments, compositions of the invention comprise an active ingredient (i.e., neomycin, Analogues, anti-angiogenic agents, and anti-neoplastic agents) that is a purified preparation.

Techniques and formulations for administering above-described compositions may be found in *Remington's Pharmaceutical Sciences,* Meade Publishing Col., Easton, Pa., latest edition.

5.3. Administration of Neomycin or Analogue

The present invention contemplates administration of pharmaceutical compositions comprising neomycin or analogue thereof to (a) inhibit the pathological angiogenesis associated with an angiogenesis-related disease, or (b) ameliorate or eliminate any other pathological symptoms of the disease. The dose of the neomycin or Analogue to be administered is a therapeutic amount effective to inhibit the formation or spread of inappropriate, undesired or excessive blood vessels at the disease site, e.g., as detected by such ability in vivo, or as extrapolated from in vitro assays (e.g., an assay that determines activity in inactivating or inhibiting the angiogenic factor-induced proliferation of endothelial cells) or from an animal model system such as the CAM assay or the corneal neovascularization assay. According to the invention, neomycin or Analogue may be administered in a single dose, or sustained administration, e.g., by intravenous (IV) drip or pump, or multiple doses.

Where the administration is in form of multiple doses, it should be at a frequency that is effective to inhibit the formation or spread of inappropriate, undesired or excessive blood vessels at the disease site, e.g., as detected by such ability in vivo, or as extrapolated from in vitro assays (e.g., an assay that determines activity in inactivating or inhibiting the angiogenic factor-induced proliferation of endothelial cells) or from an animal model system such as the CAM assay or the corneal neovascularization assay.

The present invention contemplates a daily dosage of neomycin or Analogue from about 0.5 $\mu$g/kg body weight/day to about 0.1 gm/kg body weight/day when the composition of the invention is administered orally, and from about 0.5 $\mu$g/kg body weight/day to about 0.06 gm/kg body weight/day when the composition is administered parenterally.

Where the subject being treated is human, in one embodiment of the present invention, neomycin is administered orally to the subject in divided doses totalling from about 4 Gm to about 8 Gm per day; in another embodiment, neomycin is administered intramuscularly to the subject using a daily dose of about 1 to about 6 Gm; in another embodiment, neomycin is administered parenterally to the subject using a dosage of 6 Gm or less.

The schedule of the neomycin or Analogue treatment should be at a periodicity that is sufficient to inhibit the formation or spread of inappropriate, undesired or excessive blood vessels at the disease site, and allows the subject to partially or completely recover from any undesirable side-effects caused or contributed to by the neomycin or Analogue treatment.

The duration of the neomycin or Analogue treatment should be for the length of time sufficient to inhibit the formation or spread of inappropriate, undesired or excessive blood vessels at the disease site, or preferably to cure the angiogenesis-related disease. The present invention contemplates a duration of treatment from one day up to several months.

The choice of the particular composition, form for administration, and effective dosages, as well as the frequency, schedule and duration of treatment will vary depending in part on the angiogenesis-related disease being treated.

5.4. Angiogensis-Related Diseases

The present invention provides method for treating or curing angiogenesis-related diseases, which involve excessive, inappropriate or undesired angiogenesis (i.e., pathological angiogenesis). Angiogenesis-related diseases may also involve excessive, inappropriate or undesired proliferation and/or migration of endothelial cells. Many diseases are associated with, or based on pathological angiogenesis or proliferation of endothelial cells. Angiogenesis-related diseases are myriad and varied. They include, but are not limited to, various forms of neovacularization or hypervascularization diseases, inflammatory diseases, arthritis and cancer.

As contemplated by the present invention, many solid and blood-borne tumors are angiogenesis-related diseases and are susceptible to treatment by the method of the invention. Solid tumors that may be treated by the method of the invention include, but are not limited to sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and benign solid tumors such as acoustic neuroma, neurofibroma, trachoma and pyogenic granulomas.

Blood-borne tumors such as leukemias that are susceptible to treatment by the method of the invention include, but are not limited to, acute lymphocytic leukemia and acute myelocytic leukemia (myeloblastic, promyelocytic, myelomonocytic, monocytic and erythroleukemia); chronic leukemia (chronic myelocytic [granulocytic] leukemia and chronic lymphocytic leukemia); and polycythemia vera, lymphoma (Hodgkin's disease and non-Hodgkin's disease), multiple myeloma, Waldenström's macroglobulinemia, and heavy chain disease.

Many corneal diseases involve pathological neovascularization, and hence are angiogenesis-related diseases and susceptible to treatment by the method of the invention. Such corneal neovascularization diseases include, but are not limited to, acne rosacea, atopic keratitis, bacterial ulcers, chemical burns, contact lens overwear, corneal graft rejection, diabetic retinopathy, epidemic keratoconjunctivitis, fungal ulcers, Herpes simplex infections, Herpes zoster infections, Kaposi sarcoma, lipid degeneration, marginal keratolysis, mycobacteria infections, Mooren ulcer, neovascular glaucoma and retrolental fibroplasia, periphigoid radial keratotomy, phylectenulosis, polyarteritis, protozoan infections, pterygium keratitis sicca, retinopathy of prematurity, rheumatoid arthritis, sjogrens, scleritis, Steven's Johnson disease, superior limbic keratitis, syphilis, systemic lupus, Terrien's marginal degeneration, trauma, Vitamin A deficiency, and Wegeners sarcoidosis.

Similarly, many retinal/corneal diseases also involve pathological neovascularization, and thus are also angiogenesis-related diseases that are susceptible to treatment by the method of the invention. Such diseases include, but are not limited to, artery occlusion, Bechets disease, Bests disease, chronic retinal detachment, chronic uveitis/vitritis, carotid obstructive disease, diabetic retinopathy, Eales disease, hyperviscosity syndromes, infections causing a retinitis or choroiditis, Lyme's disease, macular degeneration, mycobacterial infections, optic pits, Pagets disease, pars planitis, post-laser complications, presumed ocular histoplasmosis, pseudoxanthoma elasticum, retinopathy of prematurity, sickle cell anemia, sarcoid, Stargarts disease, syphilis, systemic lupus erythematosis, toxoplasmosis, trauma, and vein occlusion. Other such diseases include, but are not limited to, diseases associated with rubeosis and diseases caused by the abnormal proliferation of fibrovascular or fibrous tissue including all forms of proliferative vitreoretinopathy, whether or not associated with diabetes.

Many chronic inflammatory diseases also involve pathological angiogenesis, and thus can be treated by the method of the present invention. Such diseases include, but are not limited to, inflammatory bowel diseases such as Crohn's disease and ulcerative colitis, psoriasis, rheumatoid arthritis, and sarcoidosis.

Other diseases that involve pathological angiogenesis include hemangiomas, Osler-Weber-Rendu disease, or hereditary hemorrhagic telangiectasia, and acquired immune deficiency syndrome.

Accordingly, subjects having angiogenesis-related diseases would also benefit from therapeutic treatment with the method of the invention.

The invention can be better understood by referring to the following examples, which are provided merely by way of exemplification and are not intended to limit the invention.

6. EXAMPLES

6.1. Neomycin Inhibits Angiogenin-Induced Angiogenesis

This set of experiments demonstrates that the aminoglycoside antibiotic neomycin, a known PLC inhibitor, is a potent inhibitor of both nuclear translocation of angiogenin, as well as angiogenin-induced cell proliferation and angiogenesis. The results indicate that neomycin is a new type of anti-angiogenic agent that may serve in the clinical treatment of angiogenesis-related diseases.

6.1.1. Materials and Methods

6.1.1.1. Materials

Human angiogenin (Met-1) was a recombinant product from an *Escherichia coli* expression system (Shapiro et al., 1988, Anal. Biochem. 175:450–461). Fertilized chicken eggs were from Spafas. Neomycin, amikacin, gentamicin, kanamycin, paromomycin, streptomycin, penicillin, amoxicillin, bacitracin, erythromycin, staurosporine, oxophenylarsine, yeast tRNA, and ribonuclease-free BSA were from Sigma Chemicals Co; U-73122 and U-73343 were from CalBiochem; genistein was from ICC; basic fibroblast growth factor (bFGF) was from Promega; human endothelial serum-free medium (HE-SFM) was from GIBCO/BRL-Life Technologies; fetal bovine serum (FBS) was from Hyclone; excellulose GF-5 desalting columns and Iodo-Beads iodination reagents were from Pierce; methyl-[$^3$H]-thymidine (6.7 Ci/mmol, 1 Ci=37 Gbq) and Na$^{125}$I (17.4 Ci/mg) were from Dupont/NEN.

6.1.1.2. Cell Culture

Human umbilical vein endothelial (HUVE) cells were purchased from Cell Systems Corp. (Kirkland, Wash.). The cells were cultured in HE-SFM supplemented with 10% FBS and 10 ng/ml bFGF at 37° C. under 5% humidified $CO_2$ and were split 1:3 for subculture. Cells between passages 5 and 12 inclusive were used for all experiments. Cell numbers were determined with a Coulter counter, and cell viability was measured by trypan blue dye exclusion assay.

6.1.1.3. Iodination of Angiogenin $^{125}$I-labeled angiogenin was prepared with the use of Iodo-Beads as described previously (Hu et al., 1997, Proc. Natl. Acad. Sci. USA 94:2204–2209). The specific activity of $^{125}$I-angiogenin used in the experiments ranged from 1–2×10$^6$ cpm/μg.

6.1.1.4. Nuclear Translocation

HUVE cells were seeded at $5 \times 10^3$ cells/cm$^2$ in 35 mm dishes and cultured in HE-SFM supplemented with 20 ng/ml bFGF at 37° C. under 5% humidified $CO_2$ for 24 hr. The cells were washed three times with prewarmed (37° C.) HE-SFM and incubated with $^{125}$I-angiogenin (1 μg/ml) at 37° C. for 30 min. Two procedures were used to examine the effect of inhibitors on nuclear translocation. The first was to premix the inhibitors with 125I-angiogenin and adjust the sample volume to 10 μl with HE-SFM before addition to the cells. The second was to pretreat the cells in HE-SFM with the inhibitors for 10 to 30 min before $^{125}$I-angiogenin was added to the cells. After incubation, the dishes were cooled at 4° C. for 10 min and the medium was removed. The cells were washed three times with cold phosphate-buffered saline (PBS), detached by scraping, and centrifuged at 800×g for 5 min. The cells were washed once with PBS and lysed by 0.5% Triton X-100 in PBS. The nuclear fraction was isolated by centrifugation at 1200×g for 5 min. Radioactivity was determined with a gamma counter.

6.1.1.5. Cell Proliferation

HUVE cells were seeded at $4 \times 10^3$ cells/cm$^2$ in attachment factor (Cell Systems Corp.)-coated 35 mm dishes in HE-SFM, and incubated with 1 μg/ml angiogenin in the presence or absence of inhibitors at 37° C. for 48 hr. Cell were detached by trypsinization and cell numbers were determined with a Coulter counter.

6.1.1.6. Ribonucleolytic Activity Assay

The effect of neomycin on the ribonucleolytic activity of angiogenin was examined with yeast tRNA as the substrate. Angiogenin, or its mixture with neomycin was added to an assay mixture containing 0.6 mg of yeast tRNA, 30 μg of ribonuclease-free BSA, 30 mM HEPES, pH 6.8, and 30 mM NaCl in a final volume of 300 μl. After incubation for 2 hr at 37° C., 700 pl of 3.4% ice-cold perchloric acid was added, the mixture was vortexed, kept on ice for 10 mm and centrifuged at 15,000×g for 10 min at 4° C. The absorbance of the supernatants was measured at 260 nm.

6.1.1.7. Angiogenesis Assay

Angiogenesis was measured on the CAM by the method of Knighton et al. (Knighton et al., 1977, Br. J. Cancer 35:347–356) essentially as described (Fett et al., 1985, Biochemistry 24:5480–5486). Fertilized chicken eggs were kept at 18° C. for 2 days and then incubated in a humidified environment at 37° C. for 3 days. Albumin was aspirated from the embryos and after 24 hours, a "window" was cut through the shell and covered with clear tape. The embryos were incubated for another 6 days at 37° C. before an angiogenic factor and/or neomycin were applied. The angiogenic factor and/or neomycin each in about 5 μl of $H_2O$ were applied to sterile, Thermanox 15-mm disks, dried under laminar flow, and applied to the CAM surface sample side down. After 48–68 hours at 37° C., the growth of blood vessels was observed microscopically and recorded as either positive or negative. A positive response (i.e., an angiogenic response) has a typical "spokewheel" appearance.

6.1.2. Results

6.1.2.1. Neomycin Inhibits Nuclear Translocation of Angiogenin

Exogenously added angiogenin is rapidly taken up and translocated to the nucleus of proliferating endothelial cells (Moroianu et al., 1994, Proc. Natl. Acad Sci. USA 91:1677–1681). The mechanism of translocation is not yet known; but it seems to be energy and temperature dependent, suggesting the involvement of receptor-mediated endocytosis (Moroianu et al., 1994, Proc. Natl. Acad Sci. USA 91:1677–1681). Angiogenin also induces DNA synthesis and cell proliferation of sparsely cultured human endothelial cells (Hu et al., 1997, Proc. Natl. Acad. Sci. USA 94:2204–2209). Accordingly, the relationship of signal transduction and nuclear translocation was investigated by examining the effect of specific inhibitors of enzymes thought to be involved in the signal transduction process on the nuclear translocation of angiogenin in HUVE cells. As shown in Table 1, genistein and oxophenylarsine, inhibitors of tyrosine kinase and phosphotyrosine phosphatase (Mayer et al., 1995, J. Pharm. Exp. Therap. 274:427–436), respectively, have no effect on nuclear translocation of $^{125}$I-angiogenin. Staurosporine, an inhibitor of protein kinase C, at its optimal concentration of 100 nM (Mayer et al., 1995, J. Pharm. Exp. Therap. 274:427–436), was only marginally inhibitory. However, 100 μM neomycin, an aminoglycoside antibiotic and a PLC inhibitor (Somjen et al., 1997, J. Cell. Biochem. 65:53–66, Hildebrandt et al., 1997, Bri. J. Phar. 120:841–8S0), decreased the amount of $^{125}$I-angiogenin accumulated in the cell nucleus after 30 min incubation by up to 60%. Another inhibitor of PLC, U-73122, also showed significant inhibition of nuclear translocation of $^{125}$I-angiogenin (30% inhibition at 10 μM), whereas, its inactive analogue, U-73343, had no effect. These data indicate that inhibitors of PLC inhibit nuclear translocation of angiogenin in HUVE cells, implying that PLC activity is required for translocation.

TABLE 1

Inhibition of Nuclear Translocation of Angiogenin

| Inhibitors | Nuclear $^{125}$I-angiogenin (cpm) | % inhibition |
| --- | --- | --- |
| Control | 3090 ± 260 | 0 |
| Genistein (100 μM) | 3300 ± 170 | 0 |
| Oxophenylarsine (10 μM) | 3040 ± 70 | 0 |
| Staurosporine (100 nM) | 2710 ± 70 | 12 |
| Neomycin (100 μM) | 1230 ± 60 | 60 |
| U-73122 (10 μM) | 2140 ± 30 | 31 |
| U-73343 (10 μM) | 2890 ± 100 | 6 |

HUVE cells, 50,000 per 35 mm dish, were treated with inhibitors at 37° C. for 30 min $^{125}$I-angiogenin was added to a final concentration of 1 μg/ml and incubated at 37° C. for 30 min.
Nuclear fractions were isolated and radioactivities determined.

Neomycin inhibits nuclear translocation of angiogenin in a dose-dependent manner (FIG. 1). Increasing concentration of neomycin progressively decrease the amount of nuclear accumulated $^{125}$I-angiogenin from 3090±260 cpm in the control to 420±100 cpm in the presence of 500 μM inhibitor. The inhibition is not linear. At 10 μM, nuclear translocation is already inhibited by 42%. Increasing the concentration to 200 μM only increases inhibition by another 23%. Nuclear translocation cannot be completely abolished by neomycin. At 500 μM, the amount of $^{125}$I-angiogenin that accumulates in the nucleus is 14% of that in the control.

6.1.2.2. Neomycin Inhibits Angiogenin-Induced Cell Proliferation

Exogenous angiogenin stimulates DNA synthesis and cell proliferation of sparsely cultured human endothelial cells (Hu et al., 1997, Proc. Natl. Acad. Sci. USA 94:2204–2209). Since neomycin inhibits nuclear translocation of angiogenin, the inhibitor's effect on angiogenin-induced cell proliferation was examined. When cells were cultured under the conditions described, essentially all were recovered after 48 hr in the absence of angiogenin and neomycin. In the presence of 1 μg/ml angiogenin, cell number after 48 hr increased by 35%. Neomycin alone neither induced nor inhibited cell proliferation. However, it inhibited angiogenin-induced cell proliferation in a dose-dependent but non-linear manner. Thus, 5 $\mu$M neomycin already inhibited the proliferative activity of angiogenin by 49% (FIG. 2). Increasing the neomycin concentration to 25 $\mu$M inhibited angiogenin-induced cell proliferation by 69% and at 50 $\mu$M, it was completely abolished.

6.1.2.3. Neomycin Inhibits Angiogenin-Induced Angiogensis

The ability of neomycin to inhibit angiogenin-induced angiogenesis was tested in the CAM assay. As shown in Table 2, neomycin itself at the concentration ranging from about 5 to about 50 $\mu$M (20 to 200 ng in the 5 $\mu$l volume applied) does not induce angiogenesis, nor does it cause necrosis or any other visible adverse effect on the chick embryo. Angiogenin alone at 10 ng induced a positive response in 55% of the chick embryos, consistent with previous results (Fett et al., 1985, Biochemistry 24:5480–5486). Neomycin at 4 ng decreased the number of angiogenic responses induced by 10 ng angiogenin from 55% to 40%, and at 20 ng decreased it to 20%, the same percentage obtained with water control. Thus, a dose of 20 ng neomycin/embryo or higher completely inhibits angiogenin-induced angiogenesis.

TABLE 2

Effect of Neomycin on the Activity of Angiogenin in the CAM Assay

| Samples | Total Embryos | % Positive |
| --- | --- | --- |
| Angiogenin (10 ng) | 76 | 55 |
| Neomycin (20 ng) | 50 | 20 |
| Neomycin (200 ng) | 29 | 21 |
| Angiogenin (10 ng) + Neomycin (4 ng) | 40 | 40 |
| Angiogenin (10 ng) + Neomycin (20 ng) | 40 | 20 |
| Angiogenin (10 ng) + Neomycin (200 ng) | 20 | 25 |
| Water | 128 | 20 |

Data were combined from multiple sets of experiments each using between 10 and 20 embryos.

6.1.2.4. Neomycin's Effect on the Ribonucleolytic Activity of Angiogenin

The effect of neomycin on the ribonucleolytic activity of angiogenin was examined with yeast tRNA as the substrate. The ribonucleolytic activity of angiogenin in the presence of 5 $\mu$M, 10 $\mu$M, and 50 $\mu$M neomycin was 87%, 105% and 88% of that of the control. At higher concentrations, neomycin forms precipitates with tRNA. These results show that neomycin does not inhibit the cleavage of yeast tRNA by angiogenin even at a concentration of 50 $\mu$M when the proliferative and angiogenic activities were already completely abolished. These data suggest that the inhibitory activity of neomycin on angiogenin-induced blood vessel formation is not attributable to its effect on the ribonucleolytic activity of angiogenin, but rather to its inhibition of nuclear translocation of angiogenin in endothelial cells and/or its inhibition of angiogenin-induced cell proliferation.

6.1.2.5. Effects of other Aminoglycoside Antibiotics on Angiogenin-Induced Cell Proliferation or Angiogenesis Other members of aminoglycoside antibiotic family were also examined for their ability to inhibit angiogenin-induced proliferation of endothelial cells. None of the commonly used aminoglycosides-streptomycin, kanamycin, gentamicin and amikacin-inhibited angiogenin-induced cell proliferation (Table 3). Significantly, paromomycin, which differs from neomycin only at position 6 of the glucose ring, did not inhibit angiogenin-induced cell proliferation. Thus, a single substitution of —NH$_2$ by —OH renders the aminoglycoside completely inactive as an anti-angiogenin agent. Data from CAM assay indicate that amikacin and streptomycin do not inhibit angiogenin-induced angiogenesis.

TABLE 3

Effects of Aminoglycoside Antibiotics on Angiogenin-induced Cell Proliferation

| Aminoglycosides (100 $\mu$M) | Angiogenin (1 $\mu$g/ml) | Cell number | %* |
| --- | --- | --- | --- |
| None | − | 52,000 ± 100 | 120 |
|  | + | 62,500 ± 100 |  |
| Neomycin | − | 52,700 ± 700 | 101 |
|  | + | 53,400 ± 1,900 |  |
| Amikacin | − | 51,700 ± 200 | 118 |
|  | + | 61,000 ± 400 |  |
| Streptomycin | − | 51,900 ± 1,300 | 115 |
|  | + | 59,900 ± 900 |  |
| Kanamycin | − | 48,800 ± 400 | 121 |
|  | + | 58,900 ± 200 |  |
| Gentamicin | − | 45,700 ± 500 | 121 |
|  | + | 55,700 ± 900 |  |
| Paromomycin | − | 50,900 ± 500 | 116 |
|  | + | 58,900 ± 400 |  |

*percent of cell number in the presence of 1 $\mu$g/ml angiogenin relative to the corresponding control.

6.1.3. Discussion

Neomycin, an aminoglycoside, is an antibiotic that inhibits translation by binding to the small subunit of prokaryotic ribosomes causing misreading of mRNA. Unlike its structurally related compound, geneticin (G-418), which is known to bind the 80S ribosomes and block protein synthesis in eukaryotic cells and is therefore useful as a selective marker for gene transfection in eukaryotic cells (Southern et al., 1982, J. Mol. Appl. Genet. 1:327–341), neomycin does not bind to eukaryotic ribosomes. Neomycin up to 200 $\mu$M exhibited no cytotoxicity against HUVE cells. The cytotoxicity of other members of the aminoglycoside antibiotic family have also been examined. Such other aminoglycoside antibiotics, including amikacin, streptomycin, kanamycin, gentamicin and paromomycin, also exhibited no cytotoxicity against HUVE cells.

Among these aminoglycoside antibiotics, neomycin is the only one which shows inhibitory activity to angiogenin-induced cell proliferation. It is noteworthy that the structurally very similar aminoglycoside, paromomycin, has no inhibitory activity at all. Thus, the amino group on the carbon 6 of the glucose ring of neomycin apparently plays an important role in its inhibition of angiogenin-induced cell proliferation and angiogenesis.

Inhibition of nuclear translocation of angiogenin by neomycin is at least one of the reasons which lead to the inhibition of angiogenin-induced cell proliferation and angiogenesis. The concentrations required to inhibit nuclear translocation and cell proliferation by 50% are about 50 $\mu$M and 10 $\mu$M, respectively. Therefore, it is possible that some other functional aspects of neomycin, which remain to be investigated, may also contribute to its anti-angiogenesis activity.

Nuclear translocation of angiogenin in endothelial cells is thought to involve receptor-mediated endocytosis (Moroianu et al., 1994, Proc. Natl. Acad Sci. USA 91:1677–1681). However, binding of angiogenin to its surface receptor and the subsequent internalization do not seem to be inhibited by neomycin. Actually, neomycin induces a concomitant increase of cytosolic $^{125}$I-angiogenin with the decrease of nuclear $^{125}$I-angiogenin. If the PLC-inhibiting activity of neomycin is responsible for the inhibition of nuclear translocation of angiogenin, these results suggest that PLC activity is required for the steps subsequent to internalization in the nuclear translocation process. Since angiogenin activates PLC activity in endothelial cells (Bicknell et al., 1988, Proc. Natl. Acad Sci. USA 85:5961–5965) and PLC activity in turn is needed for nuclear translocation, the two cellular events may be interrelated and coordinate to function for the ultimate activity of angiogenin in endothelial cells. It is known that several cellular signal pathways activated by ligands binding to their receptors often crosstalk to obtain optimal cellular function (Jans, D. A., 1994, FASEB J. 8:841–847; Hopkins, C. R., 1994, Biochem. Pharma. 47:151–154).

Genistein, oxophenylarsine and staurosporine, which are inhibitors of tyrosine kinase, phosphotyrosine phosphatase and protein kinase C, respectively, do not inhibit nuclear translocation of angiogenin. It is unknown at present whether or not they inhibit angiogenin-induced proliferation and angiogenesis. If they do, the mechanisms would be different from that by which neomycin exerts its anti-angiogenesis effects.

The results disclosed here indicate that neomycin inhibits angiogenin-induced angiogenesis, mainly through its inhibition of nuclear translocation of angiogenin in endothelial cells. The data demonstrates that neomycin and its analogues are a new class of compounds having therapeutic use for treating angiogenesis-related diseases.

6.2. Neomycin Inhibits Nuclear Translocation of Other Angiogenic Factors

The following experiments demonstrate that neomycin inhibits nuclear translocation of angiogenic factors other than angiogenin.

6.2.1. Methods

Inhibition of nuclear translocation of angiogenic factors in HUVE cells was performed in the following manner. HUVE cells, passage 9 to 12, were cultured at 50,000 cells per 35 mm dish in HE-SFM supplemented with 20 ng/ml bFGF at 37° C. for 24 hr. The cells were washed 3 times with prewarmed HE-SFM and treated with neomycin at various concentrations at 37° C. for 10 min. $^{125}$I-bFGF, $^{125}$I-aFGF or $^{125}$-EGF, 50 ng/ml, was added and incubated at 37° C. for 30 min. At the end of incubation, the cells were cooled at 4° C. for 10 min and washed 3 times with cold PBS (4° C.), detached by scraping and centrifuged at 800×g for 5 min. The cell pellet was washed once with PBS and lysed with 0.5% triton X-100 in PBS. Nuclear fraction was isolated by centrifugation at 1200×g for 5 min. Radioactivity in the nuclear fraction was determined with a gamma counter.

6.2.2. Results

As shown in Table 4, neomycin inhibits nuclear translocation of bFGF, aFGF and EGF in HUVE cells in a dose-dependent manner. Neomycin's activity in inhibiting nuclear translocation of these three angiogenic factors in HUVE cells is not as strong as its activity against the translocation of angiogenin (see Section 6.1.2.1, supra). At 10 μM, neomycin achieved 42% inhibition of the nuclear translocation of angiogenin, but only 13% and 15% inhibition of translocation of bFGF and aFGF, respectively. Nuclear translocation of EGF was not inhibited by neomycin until the latter's concentration exceeded 100 μM. However, since nuclear translocation of angiogenic proteins in endothelial cells is absolutely required for angiogenesis to occur, these lesser inhibitory activities are still sufficient in suppressing angiogenesis induced by these angiogenic factors (see Section 6.4, infra).

TABLE 4

Neomycin Inhibits Nuclear Translocation of FGFs and EGF

| Neomycin (μM) | bFGF Counts (cpm) | % Inhib. | aFGF Counts (cpm) | % Inhib. | EGF Counts (cpm) | % Inhib. |
|---|---|---|---|---|---|---|
| 0 | 18300 ± 200 | — | 7800 ± 100 | — | 140 ± 20 | — |
| 10 | 15900 ± 100 | 13 | 6600 ± 100 | 15 | 140 ± 20 | 0 |
| 50 | 14300 ± 100 | 22 | 5800 ± 100 | 26 | 140 ± 20 | 0 |
| 100 | 13500 ± 300 | 26 | 5300 ± 100 | 32 | 130 ± 30 | 7 |
| 150 | 12400 ± 200 | 32 | 4800 ± 100 | 38 | 120 ± 10 | 14 |
| 200 | 10900 ± 100 | 40 | 4500 ± 200 | 43 | 100 ± 20 | 29 |

6.3. Neomycin Inhibits Cell Proliferation Induced By Other Angiogenic Factors

These experiments demonstrate that neomycin inhibits cell proliferation induced by angiogenic factors other than angiogenin.

6.3. 1. Methods

Effect of neomycin on cell proliferation induced by angiogenic factors was performed in the following manner. HUVE cells, passage 8, were plated on attachment factor-coated 35 mm dish in HE-SFM at a density of 3000 cells/cm$^2$. bFGF (10 ng/ml), aFGF (10 ng/ml), EGF (5 ng/ml) or VEGF (5 ng/ml) was added to the cells in the absence or presence of neomycin at different concentration immediately after the cells were seeded. The cells were incubated at 37° C. under humidified air containing 5% $CO_2$ for 48 hrs. At the end of the incubation, the cells were washed once with PBS and detached by trypsinization. Cell numbers were determined with a Coulter counter.

6.3.2. Results

As shown in Table 5, proliferation of HUVE cells induced by bFGF, aFGF and EGF was inhibited by neomycin in a dose-dependent manner. Thus, the proliferative activity of bFGF, aFGF and EGF was inhabited by 100 μM neomycin by 41%, 50% and 59%, respectively. As shown in Section 6.1.2.2., supra, neomycin inhibits angiogenin-induced proliferation of HUVE cells with an $IC_{50}$ value of <10 μM. It appears that neomycin is a more potent and specific inhibitor for angiogenin than for the other angiogenic factors. VEGF is an angiogenic factor which has not been reported to undergo nuclear translocation in endothelial cells. Neomycin only has a small effect on VEGF-induced cell proliferation. Marginal inhibition (20%) was observed at 50 μM of neomycin. At 50 μM of neomycin, angiogenin-induced cell proliferation was already completely abolished. It is noteworthy that neomycin is not an effective inhibitor of cell proliferation induced by VEGF as it is of the proliferation induced by other angiogenic factors that have been tested. These results provides further evidence to support the hypothesis that neomycin inhibits angiogenesis, especially angiogenin-induced angiogenesis, via its inhibition of nuclear translocation of the angiogenic factors in endothelial cells.

TABLE 5

Inhibition of Cell Proliferation by Neomycin

| Neomycin (μM) | Control Cell No. | bFGF Cell No. | Inhib. % | aFGF Cell No. | Inhib. % | EGF Cell No. | Inhib. % | VEGF Cell No. | Inhib. % |
|---|---|---|---|---|---|---|---|---|---|
| 0 | 31400 ± 400 | 59600 ± 2600 | — | 73900 ± 2500 | — | 5300 ± 300 | — | 45100 ± 200 | — |
| 25 | 29800 ± 300 | 51500 ± 700 | 19 | 60000 ± 400 | 25 | 46700 ± 600 | 17 | 41000 ± 300 | 14 |
| 50 | 28800 ± 1000 | 45900 ± 1200 | 34 | 51300 ± 400 | 42 | 41700 ± 600 | 35 | 38900 ± 1300 | 20 |
| 100 | 27900 ± 500 | 42600 ± 200 | 41 | 46700 ± 800 | 50 | 35700 ± 1100 | 59 | 36400 ± 400 | 22 |
| 150 | 27400 ± 200 | 39900 ± 125 | 49 | 41000 ± 1000 | 63 | 32800 ± 200 | 71 | 35000 ± 200 | 36 |
| 200 | 26300 ± 400 | 34600 ± 400 | 64 | 37500 ± 200 | 68 | 26000 ± 900 | 100 | 33800 ± 200 | 34 |

6.4. Neomycin Inhibits Angiogenesis Induced By Other Angiogenic Factors

These experiments demonstrate that neomycin inhibits angiogenesis induced by other angiogenic factors.

6.4.1. Methods

The ability of neomycin to inhibit bFGF-, CFGF-, EGF-, and VEGF-induced angiogenesis was tested in the CAM assay in a similar manner as described for angiogenin in Section 6.1.1.7, above.

6.4.2. Results

As shown in Table 6, aFGF, bFGF, and EGF, at 10 ng per egg, induced angiogenesis in 73, 78, and 69% of the eggs, respectively. The percentages of positive eggs induced by the same concentration of these three angiogenic factors in the presence of 20 ng neomycin were 36, 45, and 60%, respectively, representing an inhibition of their angiogenic activity by 71, 58, and 19%, respectively. In the presence of 200 ng neomycin, the percentage of positive eggs were 32, 34, and 30%, not significantly different from that of the water control (21%) tested simultaneously. Neomycin did not significantly inhibit the angiogenic activity of VEGF. In the absence or presence of 200 ng and 1 μg neomycin, 10 ng of VEGF induced angiogenesis in 63, 58, and 52% of the eggs. Neomycin abolishes the angiogenic activity of angiogenin (10 ng) at a dose as low as 20 ng per egg (Section 6.1.2.3, above). Thus, neomycin inhibits angiogenesis induced by angiogenin, aFGF, bFGF and EGF, but not that stimulated by VEGF.

TABLE 6

Effect of neomycin on aFGF-, bFGF-, EGF- and VEGF-induced angiogenesis in CAM assay.

| Sample | Neomycin (ng) | Total eggs | Positive eggs | % Positive | % Inhibition[a] |
|---|---|---|---|---|---|
| aFGF (10 ng) | 0 | 49 | 36 | 73 | — |
| " | 20 | 14 | 5 | 36 | 71 |
| " | 200 | 47 | 16 | 34 | 75 |
| bFGF (10 ng) | 0 | 37 | 29 | 78 | — |
| " | 20 | 33 | 15 | 45 | 58 |
| " | 200 | 38 | 12 | 32 | 81 |
| EGF (10 ng) | 0 | 26 | 18 | 69 | — |
| " | 20 | 15 | 9 | 60 | 19 |
| " | 200 | 30 | 9 | 30 | 81 |
| VEGF (10 ng) | 0 | 27 | 17 | 63 | — |
| " | 200 | 24 | 14 | 58 | 10 |
| " | 1000 | 27 | 14 | 52 | 24 |

TABLE 6-continued

Effect of neomycin on aFGF-, bFGF-, EGF- and VEGF-induced angiogenesis in CAM assay.

| Sample | Neomycin (ng) | Total eggs | Positive eggs | % Positive | % Inhibition[a] |
|---|---|---|---|---|---|
| water[b] | 0 | 212 | 45 | 21 | — |
| | 20 | 50 | 10 | 20 | — |
| | 200 | 29 | 6 | 21 | — |
| | 1000 | 13 | 3 | 23 | — |

Angiogenesis was measured on the chorioallantoic membrane as described above in Section 6.1.1.7. Growth of blood vessels was observed microscopically and recorded as either positive or negative after 48 hr of incubation. Data were combined from multiple sets of experiments each using between 10 and 20 eggs.

The angiogenic activity of VEGF in the chick CAM was not significantly inhibited by neomycin. The level of angiogenic response induced by 10 ng VEGF in the presence of 200 ng and 1 μg neomycin per embryo was 58% and 52%, respectively, not much different from that in the absence of neomycin (63%). These data are in agreement with the results obtained in the proliferation assay where neomycin does not significantly inhibit VEGF-induced proliferation of HUVE cells.

VEGF is a pleiotropic angiogenic factor implicated in both developmental neovascularization and neoplastic angiogenesis, whereas the other angiogenic factors may be only related to disease status. Therefore, the fact that neomycin does not inhibit the angiogenic activity of VEGF may, on the one hand, reflect the finding that VEGF does not undergo nuclear translocation. On the other hand, it implies that neomycin may be a selective inhibitor of angiogenesis involved only in pathological conditions but not in the neovascularization under physiological circumstance. This is significant to the use of neomycin and its analogues as therapeutic agents for use in clinical treatment of angiogenesis-dependent disease. It indicates that the use of neomycin as an anti-angiogenic agent is specific and would not cause developmental abnormality. Neomycin, at 250 μM (1 μg in the 5 μl volume applied per embryo), did not cause necrosis or any other visible adverse effects on the chick embryo.

6.5. Other Aminoglycosides Do Not Inhibit FGF-Induced Cell Proliferations

These experiments demonstrate that other aminoglycoside antibiotics do not inhibit bFGF-induced proliferation of HUVE cells.

6.5.1. Methods

The ability of the other members of the aminoglycoside antibiotic family to inhibit bFGF-induced proliferation of HUVE cells was examined in a similar manner as for angiogenin as described in Section 6.1.1.5, above. HUVE cells, passage 9, were seeded on attachment-factor coated dishes at 50,000 cells per 35 mm dish in HE-SFM. Aminoglycoside antibiotics were added and the cells were incubated with or without ng/ml bFGF at 37° C. for 48 hr.

6.5.2. Results

As shown in Table 7, 100 $\mu$M neomycin inhibited bFGF-induced proliferation of HUVE cells by 71%. By contrast, no other members of the aminoglycoside antibiotic family tested, including streptomycin, kanamycin, gentamicin and amikacin, exhibited any significant inhibitory effect on cell proliferation induced by bFGF. These results are very similar to that obtained with angiogenin-induced cell proliferation presented in Section 6.1.2.5, supra. These data indicate that the anti-angiogenic and anti-bacterial activity of neomycin may depend on the different properties of the molecule and can be separated. It is known that the anti-bacterial function of neomycin and the other aminoglycoside antibodies is the result of binding to the 16S rRNA and inhibition of initiation of protein synthesis. The anti-angiogenic activity of neomycin may derive from its inhibition of PLC via binding to $PIP_2$, and the subsequent inhibition of nuclear translocation of angiogenic proteins. The lack of effect of other aminoglycoside antibiotics on the proliferative activity of angiogenin and bFGF further indicate that neomycin is a specific and selective inhibitor of angiogenesis.

TABLE 7

Effect of Aminoglycoside Antibiotics on bFGF-induced Cell Proliferation

| Aminoglycoside (100 $\mu$M) | Control | bFGF (10 ng/ml) Cell Numbers | % Inhibition |
|---|---|---|---|
| Control | 61300 ± 500 | 99000 ± 1000 | — |
| Neomycin | 58000 ± 1500 | 68400 ± 800 | 71 |
| Streptomycin | 62300 ± 600 | 104200 ± 400 | 0 |
| Kanamycin | 62600 ± 1100 | 98000 ± 2500 | 8 |
| Gentamicin | 61800 ± 1200 | 98400 ± 1900 | 5 |
| Amikacin | 63000 ± 900 | 97600 ± 1300 | 11 |

6.6. Neomycin Inhibits Growth of PC-3 Human Prostate Tumor Cells in Athymic Mice These experiments established that neomycin inhibits the establishment and growth of PC-3 human prostate tumor cells inoculated in athymic mice.

6.6.1. Methods

The subcutaneous tumor model in athymic mice has been used extensively to show that angiogenin antagonists such as monoclonal antibodies, its binding protein and antisense DNA, prevent the establishment of human tumor cells in mice (Olson et al., 1998, Proc. Am. Assoc. Cancer Res. 39:665A; Olson et al., 1994, Cancer Res. 54:4576–4579; Olson et al., 1995, Proc. Natl. Acad. Sci. USA 92:442–446. Olson KA et al., 1996, Proc. Am. Assoc. Cancer Res. 37:395A); none of these references, however, relate in any way to neomycin. As described below, this model is useful to examine the capacity of neomycin to delay or to prevent the establishment of PC-3 human prostate tumor cells in athymic mice.

Outbred athymic mice (6 mice per group) were injected subcutaneously with a mixture of 100 $\mu$l containing $1\times10^4$ PC-3 cells, 33 $\mu$l of basement membrane components (Matrigel), and either PBS control or neomycin at a dose of 20 mg/kg body weight. The mice received subcutaneous injections proximal to the site of the original cell inoculation of PBS control or neomycin diluted in PBS at a dose of 20 mg/kg body weight 6 times per week for 20 days, followed by injection 4 times per week for another 30 days. Mice were examined daily by palpation for the first sign of tumor appearance at which time tumor size was estimated twice weekly by caliper measurements (longest perpendicular length and width).

6.6.2. Results

As shown in FIG. 3, treatment with neomycin prevented the appearance of PC-3 tumors in 50% of the mice. By day 18, 2 of 6 mice in the control group receiving PBS developed a tumor, whereas, all of the mice in the neomycin-treated group remained tumor-free. As of day 42, only 50% of the neomycin-treated as opposed to 100% of the animals in the control group had developed tumors. The dose (20 mg/kg body weight) used in this experiment was based on the usual intramuscular dose for human use (Wintrobe et al., 1971, Harrison's Principles of Internal Medicine, 6th ed., p749). There was no evidence of toxic side effects. No changes were observed between the control and neomycin-treated mice with respect to general activity, body weight, and food and fluid intake.

PC-3 cells are the most aggressive tumor cell line and are the least responsive one among the tumor cells so far tested for anti-angiogenin therapy. Thus, because neomycin is shown herein to be effective against PC-3 cells, it is expected to be more effective toward other tumor cells that are less aggressive than PC-3 cells.

6.7. Neomycin Inhibits Establishment and Growth of MDA-MB-435 Human Breast Tumor Cells in Athymic Mice Theses experiments established that neomycin inhibits the establishment and growth of MDA-MB-435 human breast tumor cells inoculated in athymic mice.

6.7.1. Methods

An orthotopic model was chosen to evaluate the efficacy of neomycin in preventing the growth of human breast cancer cells. MDA-MA-435 human breast tumor cells, which are estrogen receptor negative, were injected directly into the mammary fat pad of athymic mice. Age-matched athymic female mice were assigned to treatment groups of 8 mice each and anesthetized with ketamine (212 mg/kg body weight) and xylazine (21.2 mg/kg body weight) given intraperitoneally and allowed to stabilize under anesthesia for 15 min. A heating pad was used to maintain their body temperature throughout the procedure to minimize stress. Betadine followed by 70% alcohol was swabbed onto the skin of the left lateral thorax. An incision of 6 mm in length was made through the skin in the area of the left lateral thorax behind the left front leg and the mammary fat pad was exposed by using gentle pressure with two fingers to separate the skin at the incision site. MDA-MB-435 human breast tumor cells were harvested by trypsinization, washed in HBSS, counted using trypan blue exclusion to determine cell viability, and 10,000 cells in a total volume of 20 $\mu$l were injected into the fat pad using a 27 gauge needle. The incision was closed with 2 drops of Vetbond veterinarian tissue adhesive and the mouse was allowed to recover on the heating pad before returning to its cage. Treatment with neomycin or with control (PBS) started on day 1 and was given intraperitoneally daily for 20 days followed by injection 4 times per week for 42 days. A dosage of 60 mg neomycin per kg body weight was used in this experiment. Mice were examined daily for tumor growth by gentle palpation of the lateral left thorax in the general area of the injection.

6.7.2. Results

As shown in FIG. 4, intraperitoneal treatment with neomycin at 60 mg/kg body weight completely inhibited the establishment of MDA-MB-435 human breast tumors in athymic mice. By day 56, all the mice in the control group (8 mice) receiving only PBS developed tumors, whereas, in the neomycin-treated group, none of the mice had tumors. There was no sign of toxic side effects at this neomycin dosage (60 mg/kg body weight) when administered intraperitoneally for 62 days.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method of inhibiting pathological angiogenesis or proliferation of endothelial cells in a subject, which method comprises administering to the subject an amount of neomycin or an analogue thereof sufficient to inhibit pathological angiogenesis or proliferation of endothelial cells.

2. The method according to claim 1, wherein the neomycin analogue is
   (a) neomycin A, neomycin B, or neomycin C;
   (b) a complex comprising neomycin A, neomycin B, or neomycin C;
   (c) an aminoglycoside having a structure substantially similar to that of neomycin A, neomycin B or neomycin C;
   (d) a chemical or biological breakdown product of neomycin A, neomycin B or neomycin C;
   (e) a derivative of neomycin A, neomycin B or neomycin C; or
   (f) a naturally-occurring precursor to neomycin A, neomycin B or neomycin C.

3. The method according to claim 2, wherein the neomycin analogue comprises a substituted-2-deoxystreptamine (2-DOS) linked to two to four sugars, wherein each sugar is a pentose or hexose.

4. The method according to claim 3, wherein the neomycin analogue is a member of the neomycin, paromomycin or lividomycin aminoglycoside family.

5. The method according to claim 4, wherein the neomycin analogue comprises a glucosyl residue attached to the 4 position of the 2-DOS moiety, which glucosyl residue comprises an amino group at each of the 2 and 6 positions.

6. The method according to claim 4, wherein the neomycin analogue comprises a 2-DOS and a 2,6-diamino-2-6-dideoxy-D-glucose attached to the 4 position of 2-DOS.

7. The method according to claim 5, wherein the neomycin analogue is nebramine, gentamine $C_1$, gentamine $C_2$, gentamine $C_{1a}$, ribostamycin, or xylostasin.

8. The method according to claim 1, wherein the neomycin analogue is an inhibitor of phospholipase C.

9. The method according to claim 1, wherein the neomycin analogue is an inhibitor of nuclear translocation of an angiogenic factor.

10. The method according to claim 1, wherein the neomycin analogue is an inhibitor of endothelial cell proliferation induced by an angiogenic factor.

11. The method according to claim 1, wherein the neomycin analogue is an inhibitor of angiogenesis in the chorioallantoic membrane of chick embryo induced by an angiogenic factor.

12. The method according to claim 9, 10, or 11, wherein the angiogenic factor is angiogenin, acidic fibroblast growth factor, basic fibroblast growth factor, epidermal growth factor, tumor growth factor-alpha, tumor growth factor-beta, tumor necrosis factor-alpha or vascular endothelial growth factor.

13. The method according to claim 1 in which the subject is a human.

14. The method according to claim 1 in which the pathological angiogenesis or proliferation of endothelial cells is associated with a disease selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acoustic neuroma, neurofibroma, trachoma and pyogenic granulomas.

15. The method according to claim 14 wherein the disease is breast cancer.

16. The method according to claim 14 wherein the disease is prostate cancer.

17. The method according to claim 1 in which the pathological angiogenesis or proliferation of endothelial cells is associated with a disease selected from the group consisting of acute lymphocytic leukemia and acute myelocytic leukemia, chronic leukemia, polycythemia vera, lymphoma, multiple myeloma, Waldenström's macroglobulinemia, and heavy chain disease.

18. The method according to claim 1 in which the pathological anziogenesis or proliferation of endothelial cells is associated with a disease selected from the group consisting of acne rosacea, atopic keratitis, chemical burns, contact lens overwear, corneal graft rejection, diabetic retinopathy, epidemic keratoconjunctivitis, fungal ulcers, Herpes simplex infections, herpes zoster infections, Kaposi sarcoma, lipid degeneration, marginal keratolysis, Mooren ulcer, neovascular glaucoma and retrolental fibroplasia, periphigoid radial keratotomy, phylectenulosis, polyarteritis, protozoan infections, pterygium keratitis sicca, retinopathy of prematurity, rheumatoid arthritis, sjogrens, scleritis, Steven's Johnson disease, superior limbic keratitis, syphilis, systemic lupus, Terrien's marginal degeneration, trauma, vitamin A deficiency, and Wegeners sarcoidosis.

19. The method according to claim 1 in which the pathological angiogenesis or proliferation of endothelial cells is associated with a disease selected from the group consisting of artery occlusion, Bechets disease, Bests disease, chronic retinal detachment, chronic uveitis/vitritis, carotid obstructive disease, diabetic retinopathy, Eales disease, hyperviscosity syndromes, retinitis, choroiditis, Lyme's disease, macular degeneration, optic pits, Pagets disease, pars planitis, post-laser complications, presumed ocular histoplasmosis, pseudoxanthoma elasticum, retinopathy of prematurity, sickle cell anemia, sarcoid, Stargarts disease, syphilis, systemic lupus erythematosis, toxoplasmosis, trauma, vein occlusion, rubeosis, and proliferative vitreoretinopathy.

20. The method according to claim 1 in which the pathological angiogenesis or proliferation of endothelial cells is associated with a disease selected from the group consisting of Crohn's disease and ulcerative colitis, psoriasis, rheumatoid arthritis, sarcoidosis, hemangiomas, Osler-Weber-Rendu disease, hereditary hemorrhagic telangiectasia, and acquired immune deficiency syndrome.

21. The method according to claim 14, 15, 16, or 17 which comprises additionally administering an anti-neoplastic agent to the subject.

22. The method according to claim 21, wherein the anti-neoplastic agent is selected from the group consisting of docetaxel, etoposide, trontecan, paclitaxel, teniposide, topotecan, vinblastine, vincristine, and vindesine, busulfan, improsulfan, piposulfan, aziridines, benzodepa, carboquone, meturedepa, uredepa, altretamine, triethylenemelamine, triethylenephosphoramide, triethylenethiophosphoramide, chlorambucil, chloraphazine, cyclophosphamide, estramustine, ifosfamide, mechlorethamine, mechlorethamine oxide hydrochloride, melphalan, novembichin, perfosfamide, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, temozolomide, aclacinomycinsa actinomycin $F_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycins, peplomycin, pirarubicin, plicamycin, porfiromycin, puromycin, streptonigrin, streptozocin, tubercidin, zinostatin, zorubicin, denopterin, edatrexate, methotrexate, piritrexim, pteropterin, Tomudex®, trimetrexate, cladribine, fludarabine, 6-mercaptopurine, thiamiprine, thioguanine, ancitabine, azacitidine, 6-azauridine, carmofur, cytarabine, doxifluridine, emitefur, enocitabune, floxuridine, fluorouracil, gemcitabine, tegafur, L-asparaginase, interferon-α, interferon-β, interferon-γ, interleukin-2, lentinan, propagermanium, PSK, roquinimex, sizofican, ubenimex, carboplatin, cisplatin, miboplatin, oxaliplatin, aceglarone, amsacrine, bisantrene, defosfamide, demecolcine, diaziquone, eflomithine, elliptinium acetate, etoglucid, fenretinide, gallium nitrate, hydroxyurea, lonidamine, miltefosine, mitoguazone, mitoxantrone, mopidamol, nitracine, pentostain, phenamet, podophyllinic acid 2-ethyl-hydrazide, procabazine, razoxane, sobuzoxane, spirogermanium, tenuzonic acid, triaziquone, 2,2', 2"trichlorotriethylamine, urethan, calusterone, dromostanolone, epitiostanol, mepitiostane, testolacone, aminoglutethimide, mitotane, trilostane, bicalutamide, flutamide, nilutamide, droloxifene, tamoxifen, toremifene, aminoglutethimide, anastrozole, fadrozole, formestane, letrozole, fosfestrol, hexestrol, polyestradiol phosphate, buserelin, goserelin, leuprolide, triptorelin, chlormadinone acetate, medroxyprogesterone, megestrol acetate, melengestrol, porfimer sodium, batimastat, and folinic acid.

23. A method of inhibiting pathological angiogenesis or proliferation of endothelial cells in a subject, which method comprises administering to the subject a therapeutic amount of (a) neomycin or an analogue thereof, and (b) an anti-angiogenic agent that is not neomycin or an analogue thereof, sufficient to inhibit pathological angiogenesis or proliferation of endothelial cells.

24. The method according to claim 23, wherein the anti-angiogenic agent is selected from the group consisting of thalidomide, 2-methoxyestradiol, endostatin, angiostatin, platelet factor-4, dextran sulfate, beta-1,3-glucan sulfate, interferon-alpha, interleukin-12, 22-oxa-1 α,25-dihydroxyvitamin $D_2$, monoclonal antibody 26-2F, monoclonal antibody 36U, peptide comprising the sequence $NH_2$-Val-Phe-Ser-Val-Arg-Val-Ser-Ile-Leu-Val-Phe-COOH (SEQ ID NO. 1), peptide comprising the sequence $NH_2$-Leu-Leu-Phe-Leu-Pro-Leu-Gly-Val-Ser-Leu-Leu-Asp-Ser-COOH (SEQ ID NO. 2), human placental ribonuclease inhibitor, peptide comprising the sequence $NH_2$-Tyr-Ser-Val-Trp-Ile-Gly-Gly-Ser-Ile-Leu-Ala-Ser-Leu-Ser-Thr-Phe-Gln-Gln-Met-Trp-Ile-Ser-Lys-COOH (SEQ ID NO. 4), peptide comprising the sequence $NH_2$-Ala-Gln-Leu-Ala-Gly-Glu-Cys-Arg-Glu-Asn-Val-Cys-Met-Gly-Ile-Glu-Gly-Arg-COOH (SEQ ID NO. 3), nucleotide comprising the sequence 5'-CGGACGAATGCTTTGATGTTGTGCTG GACCAGCGTTCATTCTCA-3' (SEQ ID NO. 5), anthracycline, 15-deoxyspergualin, D-penicillamine, eponemycin, fumagillin, AGM-1470, herbimycin A, rapamycin, CAI, CM101, and marimastat.

25. A pharmaceutical composition comprising a therapeutically effective amount of (a) neomycin or an analogue thereof, and (b) an anti-angiogenic agent that is not neomycin or an analogue thereof, together with a pharmaceutically acceptable carrier, said amount sufficient to suppress pathological angiogenesis or proliferation of endothelial cells in a subject.

26. The pharmaceutical composition of claim 25, wherein the neomycin analogue is
   (a) neomycin A, neomycin B, or neomycin C;
   (b) a complex comprising neomycin A, neomycin B, or neomycin C;
   (c) an aminoglycoside having a structure substantially similar to that of neomycin A, neomycin B or neomycin C;
   (d) a chemical or biological breakdown product of neomycin A, neomycin B or neomycin C;
   (e) a derivative of neomycin A, neomycin B or neomycin C; or
   (f) a naturally-occurring precursor to neomycin A, neomycin B or neomycin C.

27. The pharmaceutical composition of claim 26, wherein the neomycin analogue comprises a substituted-2-deoxystreptamine (2-DOS) linked to two to four sugars, wherein each sugar is a pentose or hexose.

28. The pharmaceutical composition of claim 27, wherein the neomycin analogue is a member of the neomycin, paromomycin or lividomycin aminoglycoside family.

29. The pharmaceutical composition of claim 28, wherein the neomycin analogue comprises a glucosyl residue attached to the 4 position of the 2-DOS moiety, which glucosyl residue comprises an amino group at each of the 2 and 6 positions.

30. The pharmaceutical composition of claim 29, wherein the neomycin analogue comprises a 2-DOS and a 2,6-diamino-2-6-dideoxy-D-glucose attached to the 4 position of 2-DOS.

31. The pharmaceutical composition of claim 29, wherein the neomycin analogue is nebramine, gentamine $C_1$, gentamine $C_2$, gentamine $C_{1a}$, ribostamycin, or xylostasin.

32. The pharmaceutical composition of claim 25, wherein the neomycin analogue is an inhibitor of nuclear translocation of an angiogenic factor.

33. The pharmaceutical composition of claim 25, wherein the neomycin analogue is an inhibitor of phospholipase C.

34. The pharmaceutical composition of claim 25, wherein the neomycin analogue is an inhibitor of endothelial cell proliferation induced by an angiogenic factor.

35. The pharmaceutical composition of claim 25, wherein the neomycin analogue is an inhibitor of angiogenesis in the chorioallantoic membrane of chick embryo induced by an angiogenic factor.

36. The pharmaceutical composition of claim 32, 34 or 35, wherein the angiogenic factor is angiogenin, acidic fibroblast growth factor, basic fibroblast growth factor, epidermal growth factor, tumor growth factor-alpha, tumor growth factor-beta, tumor necrosis factor-alpha, vascular endothelial growth factor, platelet-derived growth factor, platelet-derived endothelial cell growth factor, placental growth factor, hepatocyte growth factor, platelet activating factor, insulin-like growth factor, interleukin-8, or granulocyte-colony stimulating factor.

37. The pharmaceutical composition of claim 25 in which the subject is a human.

38. The pharmaceutical composition of claim 25 in which the anti-angiogenic factor is selected from the group consisting of thalidomide, 2-methoxyestradiol, endostatin, angiostatin, platelet factor-4, dextran sulfate, beta-1,3-glucan sulfate, interferon-alpha, interleukin-12, 22-oxa- 1 α, 25-dihydroxyvitamin $D_2$, monoclonal antibody 26-2F, monoclonal antibody 36U, peptide comprising the sequence $NH_2$-Val-Phe-Ser-Val-Arg-Val-Ser-Ile-Leu-Val-Phe-COOH (SEQ ID NO. 1), peptide comprising the sequence $NH_2$-Leu-Leu-Phe-Leu-Pro-Leu-Gly-Val-Ser-Leu-Leu-Asp-Ser-COOH (SEQ ID NO. 2), human placental ribonuclease inhibitor, peptide comprising the sequence $NH_2$-Tyr-Ser-Val-Trp-Ile-Gly-Gly-Ser-Ile-Leu-Ala-Ser-Leu-Ser-Thr-Phe-Gln-Gln-Met-Trp-Ile-Ser-Lys-COOH (SEQ ID NO. 4), peptide comprising the sequence $NH_2$-Ala-Gln-Leu-Ala-Gly-Glu-Cys-Arg-Glu-Asn-Val-Cys-Met-Gly-Ile-Glu-Gly-Arg-COOH (SEQ ID NO. 3), nucleotide comprising the sequence 5'-CGGACGAATGCTTTGATGTTGTGCTG GACCAGCGTTCATTCTCA-3'(SEQ ID NO. 5), anthracycline, 15-deoxyspergualin, D-penicillamine, eponemycin, fumagillin, AGM-1470, herbimycin A, rapamycin, CAI, CM101, and marimastat.

39. A pharmaceutical composition comprising a therapeutically effective amount of (a) neomycin or an analogue thereof, and (b) an anti-neoplastic agent, together with a pharmaceutically acceptable carrier, said amount sufficient to treat an angiogenesis-related disease which is a tumor in a subject.

40. The pharmaceutical composition of claim 39, wherein the neomycin analogue is
   (a) neomycin A, neomycin B, or neomycin C;
   (b) a complex comprising neomycin A, neomycin B, or neomycin C;
   (c) an aminoglycoside having a structure substantially similar to that of neomycin A, neomycin B or neomycin C;
   (d) a chemical or biological breakdown product of neomycin A, neomycin B or neomycin C;
   (e) a derivative of neomycin A, neomycin B or neomycin C; or
   (f) a naturally-occurring precursor to neomycin A, neomycin B or neomycin C.

41. The pharmaceutical composition of claim 40, wherein the neomycin analogue comprises a substituted-2-deoxystreptamine (2-DOS) linked to two to four sugars, wherein each sugar is a pentose or hexose.

42. The pharmaceutical composition of claim 41, wherein the neomycin analogue is a member of the neomycin, paromomycin or lividomycin aminoglycoside family.

43. The pharmaceutical composition of claim 42, wherein the neomycin analogue comprises a glucosyl residue attached to the 4 position of the 2-DOS moiety, which glucosyl residue comprises an amino group at each of the 2 and 6 positions.

44. The pharmaceutical composition of claim 43, wherein the neomycin analogue comprises a 2-DOS and a 2,6-diamino-2-6-dideoxy-D-glucose attached to the 4 position of 2-DOS.

45. The pharmaceutical composition of claim 43, wherein the neomycin analogue is nebramine, gentamine $C_1$, gentamine $C_2$, gentamine $C_{1a}$, ribostamycin, or xylostasin.

46. The pharmaceutical composition of claim 39, wherein the neomycin analogue is an inhibitor of nuclear translocation of an angiogenic factor.

47. The pharmaceutical composition of claim 39, wherein the neomycin analogue is an inhibitor of phospholipase C.

48. The pharmaceutical composition of claim 39, wherein the neomycin analogue is an inhibitor of endothelial cell proliferation induced by an angiogenic factor.

49. The pharmaceutical composition of claim 39, wherein the neomycin analogue is an inhibitor of angiogenesis in the chorioallantoic membrane of chick embryo induced by an angiogenic factor.

50. The pharmaceutical composition of claim 46, 48 or 49, wherein the angiogenic factor is angiogenin, acidic fibroblast growth factor, basic fibroblast growth factor, epidermal growth factor, tumor growth factor-alpha, tumor growth factor-beta, tumor necrosis factor-alpha, vascular endothelial growth factor, platelet-derived growth factor, platelet-derived endothelial cell growth factor, placental growth factor, hepatocyte growth factor, platelet activating factor, insulin-like growth factor, interleukin-8, or granulocyte-colony stimulating factor.

51. The pharmaceutical composition of claim 39 in which the subject is a human.

52. The pharmaceutic composition of claim 39, wherein the anti-neoplastic agent is selected from the group consisting of docetaxel, etoposide, trontecan, paclitaxel, teniposide, topotecan, vinblastine, vincristine, and vindesine, busulfan, improsulfan, piposulfan, aziridines, benzodepa, carboquone, meturedepa, uredepa, altretamine, triethylenemelamine, triethylenephosphoramide, triethylenethiophosphoramide, chlorambucil, chloraphazine, cyclophosphamide, estramustine, ifosfamide, mechlorethamine, mechlorethamine oxide hydrochloride, melphalan, novembichin, perfosfarmide, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, temozolomide, aclacinomycinsa actinomycin $F_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycins, peplomycin, pirarubicin, plicamycin, porfiromycin, puromycin, streptonigrin, streptozocin, tubercidin, zinostatin, zorubicin, denopterin, edatrexate, methotrexate, piritrexim, pteropterin, Tomudex®, trimetrexate, cladribine, fludarabine, 6-mercaptopurine, thiamiprine, thioguanine, ancitabine, azacitidine, 6-azauridine, carmofur, cytarabine, doxifluridine, emitefur, enocitabune, floxuridine, fluorouracil, gemcitabine, tegafur, L-asparaginase, interferon-α, interferon-β, interferon-γ, interleukin-2, lentinan, propagermanium, PSK, roquinimex, sizofican, ubenimex, carboplatin, cisplatin, miboplatin, oxaliplatin, aceglarone, amsacrine, bisantrene, defosfamide, demecolcine, diaziquone, eflornithine, elliptinium acetate, etoglucid, fenretinide, gallium nitrate, hydroxyurea, lonidamine, miltefosine, mitoguazone, mitoxantrone, mopidamol, nitracine, pentostain, phenamet, podophyllinic acid 2-ethyl-hydrazide, procabazine, razoxane, sobuzoxane, spirogermanium, tenuzonic acid, triaziquone, 2,2', 2"trichlorotriethylamine, urethan, calusterone, dromostanolone, epitiostanol, mepitiostane, testolacone, aminoglutethimide, mitotane, trilostane, bicalutamide, flutamide, nilutamide, droloxifene, tamoxifen, toremifene, aminoglutethimide, anastrozole, fadrozole, formestane, letrozole, fosfestrol, hexestrol, polyestradiol phosphate, buserelin, goserelin, leuprolide, triptorelin, chlormadinone acetate, medroxyprogesterone, megestrol acetate, melengestrol, porfimer sodium, batimastar, and folinic acid.

53. A method for selecting a neomycin analogue for use in inhibiting angiogenesis or proliferation of endothelial cells, comprising testing the neomycin analogue for activity for inhibiting angiogenesis.

54. The method according to claim 53, which comprises
(a) incubating a first culture of endothelial cells with the neomycin analogue and an angiogenic factor. in a growth medium, and incubating a second culture of endothelial cells with the angiogenic factor in the growth medium lacking the neomycin analogue, wherein the angiogenic factor is labeled;
(b) determining the amounts of angiogenic factor present in the nuclei of cells in the first and the second cultures; and
(c) selecting for use in treating the angiogenesis-related disease, the neomycin analogue that inhibits nuclear translocation of the angiogenic factor in cells of the first culture by at least 10% of the amount of the angiogenic factor translocated to the nuclei of the cells in the second culture.

55. The method according to claim 53, which comprises
(a) incubating a first culture of endothelial cells with the neomycin analogue in a growth medium, and incubating a second culture of endothelial cells in a growth medium lacking the neomycin analogue;
(b) incubating the first and the second cultures with an angiogenic factor in the growth medium, wherein the angiogenic factor is labeled;
(c) determining the amount of angiogenic factor present in the nuclei of cells in the first and the second cultures; and
(d) selecting for use in treating the angiogenesis-related disease, the neomycin analogue that inhibits nuclear translocation of the angiogenic factor in the cells of the first culture by at least 10% of the amount of nuclear translocation of the angiogenic factor in the cells of the second culture.

56. The method according to claim 53, which comprises
(a) incubating a first culture of endothelial cells with the neomycin analogue and an angiogenic factor in a growth medium, incubating a second culture of endothelial cells with the neomycin analogue in the growth medium lacking the angiogenic factor, incubating a third culture of endothelial cells with the angiogenic factor in the growth medium lacking the neomycin analogue, incubating a fourth culture of endothelial cells in the growth medium lacking the neomycin analogue and the angiogenic factor;
(b) determining the cell numbers of the first, the second, the third and the fourth cultures; and
(c) selecting for use in treating the angiogenesis-related disease, the neomycin analogue that reduces the increase in the cell number in the second culture over the cell number in the first culture to less than about 75% of the increase in cell number of the third culture over the cell number of the fourth culture.

57. The method according to claim 53, which comprises
(a) contacting the chorioallantoic membrane of a first group of chick embryos with the neomycin analogue and an angiogenic factor, contacting the chorioallantoic membrane of a second group of chick embryos with the neomycin analogue but not the angiogenic factor, contacting the chorioallantoic membrane of a third group of chick embryos with the angiogenic factor but not the neomycin analogue, and contacting the chorioallantoic membrane of a fourth group of chick embryos with a solution lacking the neomycin analogue and the antigenic factor;
(b) incubating the first, the second, the third and the fourth groups of chick embryos;
(c) determining the numbers of embryos having an angiogenic response in the first, the second, the third and the fourth groups of embryos; and
(d) selecting for use in treating the angiogenesis-related disease, the neomycin analogue that reduces the increase in the number of embryos exhibiting an angiogenic response in the second group of embryos over the number of embryos exhibiting an angiogenic response in the first group of embryos to less than about 75% of the increase in the number of embryos exhibiting an angiogenic response in the third group of embryos over the number of embryos exhibiting an angiogenic response in the fourth group of embryos.

58. The method according to any one of claims 53 to 57, wherein the neomycin analogue is
(a) neomycin A, neomycin B, or neomycin C;
(b) a complex comprising neomycin A, neomycin B, or neomycin C;
(c) an aminoglycoside having a structure substantially similar to that of neomycin A, neomycin B or neomycin C;
(d) a chemical or biological breakdown product of neomycin A, neomycin B or neomycin C;
(e) a derivative of neomycin A, neomycin B or neomycin C; or
(f) a naturally-occurring precursor to neomycin A, neomycin B or neomycin C.

59. The method according to claim 58, wherein the neomycin analogue comprises a substituted-2-deoxystreptamine (2-DOS) linked to two to four sugars, wherein each sugar is a pentose or hexose.

60. The method according to claim 59, wherein the neomycin analogue is a member of the neomycin, paromomycin or lividomycin aminoglycoside family.

61. The method according to claim 60, wherein the neomycin analogue comprises a glucosyl residue attached to the 4 position of the 2-DOS moiety, which glucosyl residue comprises an amino group at each of the 2 and 6 positions.

62. The method according to claim 61, wherein the neomycin analogue comprises a 2-DOS and a 2,6-diamino-2-6-dideoxy-D-glucose attached to the 4 position of 2-DOS.

63. The method according to any one of claims 53 to 57, wherein the angiogenic factor is angiogenin, acidic fibroblast growth factor, basic fibroblast growth factor, epidermal growth factor, tumor growth factor-alpha, tumor growth factor-beta, tumor necrosis factor-alpha, vascular endothelial growth factor, platelet-derived growth factor, platelet-derived endothelial cell growth factor, placental growth factor, hepatocyte growth factor, platelet activating factor, insulin-like growth factor, interleukin-8, or granulocyte-colony stimulating factor.

* * * * *

```
                       SEQUENCE LISTING

<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<223> OTHER INFORMATION: deduced from antisense RNA corresponding to the
      receptor-binding stie of angiogenin in 5'->3'
      direction

<400> SEQUENCE: 1

Val Phe Ser Val Arg Val Ser Ile Leu Val Phe
1               5                   10

<210> SEQ ID NO 2
<211> LENGTH: 13
<212> TYPE: PRT
<213> ORGANISM: Artificial Sequence
<220> FEATURE:
<223> OTHER INFORMATION: deduced from antisense RNA corresponding to the
      receptor-binding stie of angiogenin in 3'->5'
      direction

<400> SEQUENCE: 2

Leu Leu Phe Leu Pro Leu Gly Val Ser Leu Leu Asp Ser
1               5                   10

<210> SEQ ID NO 3
<211> LENGTH: 18
<212> TYPE: PRT
<213> ORGANISM: Homo Sapiens

<400> SEQUENCE: 3

Ala Gln Leu Ala Gly Glu Cys Arg Glu Asn Val Cys Met Gly Ile Glu
1               5                   10                  15

Gly Arg

<210> SEQ ID NO 4
<211> LENGTH: 23
<212> TYPE: PRT
<213> ORGANISM: Homo Sapiens

<400> SEQUENCE: 4

Tyr Ser Val Trp Ile Gly Gly Ser Ile Leu Ala Ser Leu Ser Thr Phe
1               5                   10                  15

Gln Gln Met Trp Ile Ser Lys
            20

<210> SEQ ID NO 5
<211> LENGTH: 44
<212> TYPE: DNA
```

-continued

```
<213> ORGANISM: Homo Sapiens

<400> SEQUENCE: 5
cggacgaatg ctttgatgtt gtgctggacc agcgttcatt ctca                    44
```